(12) United States Patent
Von Arx et al.

(10) Patent No.: US 8,271,093 B2
(45) Date of Patent: Sep. 18, 2012

(54) SYSTEMS AND METHODS FOR DERIVING RELATIVE PHYSIOLOGIC MEASUREMENTS USING A BACKEND COMPUTING SYSTEM

(75) Inventors: Jeffrey A. Von Arx, Minneapolis, MN (US); Scott T. Mazar, Woodbury, MN (US); Abhi Chavan, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1568 days.

(21) Appl. No.: 10/943,627

(22) Filed: Sep. 17, 2004

(65) Prior Publication Data

US 2006/0064143 A1 Mar. 23, 2006

(51) Int. Cl.
*A61N 1/08* (2006.01)
(52) U.S. Cl. .......................................................... 607/60
(58) Field of Classification Search ...................... 607/60
See application file for complete search history.

(56) References Cited

U.S. PATENT DOCUMENTS

| | | |
|---|---|---|
| 2,786,899 A | 3/1957 | Carlisle |
| 3,310,885 A | 3/1967 | Alderson |
| 3,320,946 A | 5/1967 | Dethloff et al. |
| 3,536,836 A | 10/1970 | Pfeiffer |
| 3,568,661 A | 3/1971 | Franklin |
| 3,672,352 A | 6/1972 | Summers |
| 3,692,027 A | 9/1972 | Ellinwood |
| 3,757,770 A | 9/1973 | Brayshaw et al. |
| 3,794,840 A | 2/1974 | Scott |
| 3,868,578 A | 2/1975 | Oldham |
| 3,943,915 A | 3/1976 | Severson |
| 4,003,379 A | 1/1977 | Ellinwood |
| 4,041,954 A | 8/1977 | Ohara |
| 4,099,530 A | 7/1978 | Chen et al. |
| 4,127,110 A | 11/1978 | Bullara |
| 4,146,029 A | 3/1979 | Ellinwood |

(Continued)

FOREIGN PATENT DOCUMENTS

EP 0928 598 12/1998

(Continued)

OTHER PUBLICATIONS

International Search Report and Written Opinion for PCT/US2005/031394, filed Sep. 1, 2005, both mailed Feb. 8, 2006.

(Continued)

*Primary Examiner* — Niketa Patel
*Assistant Examiner* — Alyssa M Alter
(74) *Attorney, Agent, or Firm* — Faegre Baker Daniels LLP

(57) ABSTRACT

One embodiment of the present invention relates to a system for deriving physiologic measurement values that are relative to ambient conditions. In one embodiment, the system comprises an implantable medical device ("IMD"), an external computing device, and a backend computing system. The IMD determines an absolute physiologic parameter value within a patient's body, and communicates the absolute physiologic parameter value outside the patient's body, for example, to the external computing device. Further, the external computing device receives the absolute physiologic parameter from the IMD and communicates it to the backend computing system. The backend computing system receives the absolute physiologic parameter value and obtains an ambient condition value outside the body that can affect the absolute physiologic parameter value. The backend computing system then calculates a relative physiologic parameter value from the ambient condition value and the absolute physiologic parameter value, and in some embodiments, stores the relative physiologic parameter value in a storage location, such as a memory or database.

32 Claims, 12 Drawing Sheets

U.S. PATENT DOCUMENTS

| | | |
|---|---|---|
| 4,223,801 A | 9/1980 | Carlson |
| 4,227,407 A | 10/1980 | Drost |
| 4,237,900 A | 12/1980 | Schulman et al. |
| 4,281,664 A | 8/1981 | Duggen |
| 4,360,019 A | 11/1982 | Portner et al. |
| 4,407,296 A | 10/1983 | Anderson |
| 4,450,527 A | 5/1984 | Sramek |
| 4,480,483 A | 11/1984 | McShane |
| 4,519,401 A | 5/1985 | Ko et al. |
| 4,541,431 A | 9/1985 | Ibrahim et al. |
| 4,543,955 A | 10/1985 | Schroeppel |
| 4,550,370 A | 10/1985 | Baker |
| 4,583,553 A | 4/1986 | Shah et al. |
| 4,585,004 A | 4/1986 | Brownlee |
| 4,593,703 A | 6/1986 | Cosman |
| 4,600,855 A | 7/1986 | Strachan |
| 4,616,640 A | 10/1986 | Kaali et al. |
| 4,651,740 A | 3/1987 | Schroeppel |
| 4,653,508 A | 3/1987 | Cosman |
| 4,660,568 A | 4/1987 | Cosman |
| 4,676,255 A | 6/1987 | Cosman |
| 4,677,985 A | 7/1987 | Bro et al. |
| 4,680,957 A | 7/1987 | Dodd |
| 4,686,987 A | 8/1987 | Salo et al. |
| 4,697,595 A | 10/1987 | Breyer et al. |
| 4,716,903 A | 1/1988 | Hansen et al. |
| 4,726,380 A | 2/1988 | Vollmann et al. |
| 4,768,176 A | 8/1988 | Kehr et al. |
| 4,768,177 A | 8/1988 | Kehr et al. |
| 4,781,715 A | 11/1988 | Wurzel |
| 4,791,936 A | 12/1988 | Snell et al. |
| 4,793,827 A | 12/1988 | Kovacs et al. |
| 4,809,697 A | 3/1989 | Causey, III et al. |
| 4,814,974 A | 3/1989 | Narayanan et al. |
| 4,845,503 A | 7/1989 | Adam et al. |
| 4,846,191 A | 7/1989 | Brockway et al. |
| 4,854,327 A | 8/1989 | Kunig |
| 4,886,064 A | 12/1989 | Strandberg |
| 4,899,752 A | 2/1990 | Cohen |
| 4,909,259 A | 3/1990 | Tehrani |
| 4,918,736 A | 4/1990 | Bordewijk |
| 4,920,489 A | 4/1990 | Hubelbank et al. |
| 4,945,477 A | 7/1990 | Edwards |
| 4,945,914 A | 8/1990 | Allen |
| 4,967,749 A | 11/1990 | Cohen |
| 4,986,270 A | 1/1991 | Cohen |
| 4,991,579 A | 2/1991 | Allen |
| 4,995,068 A | 2/1991 | Chou et al. |
| 4,995,398 A | 2/1991 | Turnidge |
| 5,002,062 A | 3/1991 | Suzuki |
| 5,003,976 A | 4/1991 | Alt |
| 5,007,431 A | 4/1991 | Donehoo, III |
| 5,024,224 A | 6/1991 | Engebretson |
| 5,025,795 A | 6/1991 | Kunig |
| 5,029,582 A | 7/1991 | Lekholm |
| 5,040,536 A | 8/1991 | Riff |
| 5,040,538 A | 8/1991 | Mortazavi |
| 5,052,399 A | 10/1991 | Olive et al. |
| 5,113,859 A | 5/1992 | Funke |
| 5,154,171 A | 10/1992 | Chirife |
| 5,161,536 A | 11/1992 | Vilkomerson et al. |
| 5,163,429 A | 11/1992 | Cohen |
| 5,178,151 A | 1/1993 | Sackner |
| 5,178,153 A | 1/1993 | Einzig |
| 5,190,035 A | 3/1993 | Salo et al. |
| 5,199,428 A | 4/1993 | Obel et al. |
| 5,200,891 A | 4/1993 | Kehr et al. |
| 5,213,098 A | 5/1993 | Bennett et al. |
| 5,215,098 A | 6/1993 | Steinhaus et al. |
| 5,217,021 A | 6/1993 | Steinhaus et al. |
| 5,246,008 A | 9/1993 | Mueller |
| 5,263,486 A | 11/1993 | Jeffreys |
| 5,267,174 A | 11/1993 | Kaufman et al. |
| 5,277,191 A | 1/1994 | Hughes |
| 5,279,309 A | 1/1994 | Taylor et al. |
| 5,279,607 A | 1/1994 | Schentag et al. |
| 5,289,821 A | 3/1994 | Swartz |
| 5,300,092 A | 4/1994 | Schaldach |
| 5,309,919 A | 5/1994 | Snell et al. |
| 5,312,446 A | 5/1994 | Holschbach et al. |
| 5,313,953 A | 5/1994 | Yomtov et al. |
| 5,314,457 A | 5/1994 | Jeutter et al. |
| 5,329,459 A | 7/1994 | Kaufman et al. |
| 5,330,505 A | 7/1994 | Cohen |
| 5,331,966 A | 7/1994 | Bennett et al. |
| 5,339,051 A | 8/1994 | Koehler et al. |
| 5,354,316 A | 10/1994 | Keimel |
| 5,360,440 A | 11/1994 | Andersen |
| 5,368,040 A | 11/1994 | Carney |
| 5,375,603 A | 12/1994 | Feiler |
| 5,394,457 A | 2/1995 | Leibinger et al. |
| 5,397,329 A | 3/1995 | Allen |
| 5,411,535 A | 5/1995 | Fujii et al. |
| 5,411,551 A | 5/1995 | Winston et al. |
| 5,417,717 A | 5/1995 | Salo et al. |
| 5,423,334 A | 6/1995 | Jordan |
| 5,438,990 A | 8/1995 | Wahlstrand et al. |
| 5,442,351 A | 8/1995 | Horspool et al. |
| 5,445,608 A | 8/1995 | Chen et al. |
| 5,454,838 A | 10/1995 | Vallana et al. |
| 5,458,627 A | 10/1995 | Baranowski, Jr. et al. |
| 5,469,859 A | 11/1995 | Tsoglin et al. |
| 5,476,488 A | 12/1995 | Morgan et al. |
| 5,488,954 A | 2/1996 | Sleva et al. |
| 5,490,962 A | 2/1996 | Cima et al. |
| 5,507,780 A | 4/1996 | Finch |
| 5,509,424 A | 4/1996 | Al-Ali |
| 5,518,001 A | 5/1996 | Snell |
| 5,528,067 A | 6/1996 | Farb |
| 5,535,752 A | 7/1996 | Halperin et al. |
| 5,545,186 A | 8/1996 | Olson et al. |
| 5,558,091 A | 9/1996 | Acker et al. |
| 5,562,714 A | 10/1996 | Grevious |
| 5,564,434 A | 10/1996 | Halperin et al. |
| 5,571,152 A | 11/1996 | Chen et al. |
| 5,603,331 A | 2/1997 | Heemels et al. |
| 5,604,531 A | 2/1997 | Iddan et al. |
| 5,619,997 A | 4/1997 | Kaplan |
| 5,623,935 A | 4/1997 | Faisandier |
| 5,626,630 A | 5/1997 | Markowitz et al. |
| 5,628,782 A | 5/1997 | Myers |
| 5,642,731 A | 7/1997 | Kehr |
| 5,643,327 A | 7/1997 | Dawson et al. |
| 5,650,770 A | 7/1997 | Schlager et al. |
| 5,656,428 A | 8/1997 | McAllister et al. |
| 5,704,352 A | 1/1998 | Tremblay et al. |
| 5,705,753 A | 1/1998 | Hastings et al. |
| 5,709,216 A | 1/1998 | Woodson, III |
| 5,728,281 A | 3/1998 | Holmstrom et al. |
| 5,729,129 A | 3/1998 | Acker |
| 5,732,708 A | 3/1998 | Nau et al. |
| 5,733,313 A | 3/1998 | Barreras, Sr. et al. |
| 5,735,887 A | 4/1998 | Barreras, Sr. et al. |
| 5,741,316 A | 4/1998 | Chen et al. |
| 5,749,909 A | 5/1998 | Schroeppel et al. |
| 5,752,235 A | 5/1998 | Kehr et al. |
| 5,752,976 A | 5/1998 | Duffin et al. |
| 5,755,766 A | 5/1998 | Chastain et al. |
| 5,769,877 A | 6/1998 | Barreras, Sr. |
| 5,772,999 A | 6/1998 | Greenblatt et al. |
| 5,776,168 A | 7/1998 | Gunderson |
| 5,776,324 A | 7/1998 | Usala |
| 5,779,634 A | 7/1998 | Ema et al. |
| 5,785,660 A | 7/1998 | van Lake et al. |
| 5,792,195 A | 8/1998 | Carlson et al. |
| 5,796,827 A | 8/1998 | Coppersmith et al. |
| 5,797,898 A | 8/1998 | Santini, Jr. et al. |
| 5,800,478 A | 9/1998 | Chen et al. |
| 5,804,258 A | 9/1998 | Lohwasser et al. |
| 5,807,258 A | 9/1998 | Cimochowski et al. |
| 5,807,395 A | 9/1998 | Mulier et al. |
| 5,807,397 A | 9/1998 | Barreras |
| 5,810,009 A | 9/1998 | Mine et al. |
| 5,810,735 A | 9/1998 | Halperin et al. |
| 5,819,740 A | 10/1998 | Muhlenberg et al. |
| 5,832,924 A | 11/1998 | Archibald et al. |
| 5,833,603 A | 11/1998 | Kovacs et al. |

| | | |
|---|---|---|
| 5,833,715 A | 11/1998 | Vachon et al. |
| 5,835,455 A | 11/1998 | Hanson et al. |
| 5,836,300 A | 11/1998 | Mault |
| 5,836,889 A | 11/1998 | Wyborny et al. |
| 5,836,982 A | 11/1998 | Muhlenberg et al. |
| 5,843,089 A | 12/1998 | Sahatjian et al. |
| 5,843,135 A | 12/1998 | Weijand et al. |
| 5,855,609 A | 1/1999 | Knapp |
| 5,856,722 A | 1/1999 | Haronian et al. |
| 5,868,673 A | 2/1999 | Vesely |
| 5,873,835 A | 2/1999 | Hastings et al. |
| 5,873,904 A | 2/1999 | Ragheb et al. |
| 5,880,661 A | 3/1999 | Davidson et al. |
| 5,886,267 A | 3/1999 | Ortiz |
| 5,891,180 A | 4/1999 | Greeninger et al. |
| 5,904,708 A | 5/1999 | Goedeke |
| 5,908,392 A | 6/1999 | Wilson et al. |
| 5,911,685 A | 6/1999 | Siess et al. |
| 5,919,221 A | 7/1999 | Miesel |
| 5,935,081 A | 8/1999 | Kadhiresan |
| 5,938,903 A | 8/1999 | Broderick |
| 5,941,249 A | 8/1999 | Maynard |
| 5,951,458 A | 9/1999 | Hastings et al. |
| 5,954,641 A | 9/1999 | Kehr et al. |
| 5,957,950 A | 9/1999 | Mockros et al. |
| 5,967,986 A | 10/1999 | Cimochowski et al. |
| 5,976,169 A | 11/1999 | Imran |
| 5,979,898 A | 11/1999 | Pan |
| 5,980,554 A | 11/1999 | Lenker et al. |
| 6,002,963 A | 12/1999 | Mouchawar et al. |
| 6,009,472 A | 12/1999 | Boudou et al. |
| 6,021,347 A | 2/2000 | Herbst et al. |
| 6,023,641 A | 2/2000 | Thompson |
| 6,024,704 A | 2/2000 | Meador et al. |
| 6,053,873 A | 4/2000 | Govari et al. |
| 6,080,190 A | 6/2000 | Schwartz |
| 6,083,248 A | 7/2000 | Thompson |
| 6,112,116 A | 8/2000 | Fischell et al. |
| 6,123,861 A | 9/2000 | Santini, Jr. et al. |
| 6,140,740 A | 10/2000 | Porat et al. |
| 6,141,588 A * | 10/2000 | Cox et al. .................... 607/9 |
| 6,152,885 A | 11/2000 | Taepke |
| 6,155,267 A | 12/2000 | Nelson |
| 6,161,032 A | 12/2000 | Acker |
| 6,162,238 A | 12/2000 | Kaplan et al. |
| 6,164,284 A | 12/2000 | Schulman et al. |
| 6,170,488 B1 | 1/2001 | Spillman, Jr. et al. |
| 6,171,252 B1 | 1/2001 | Roberts |
| 6,179,767 B1 | 1/2001 | Ziegler et al. |
| 6,185,452 B1 | 2/2001 | Schulman et al. |
| 6,185,455 B1 | 2/2001 | Loeb et al. |
| 6,185,457 B1 | 2/2001 | Kroll et al. |
| 6,198,965 B1 | 3/2001 | Penner et al. |
| 6,200,265 B1 | 3/2001 | Walsh et al. |
| 6,201,991 B1 | 3/2001 | Chekanov |
| 6,206,914 B1 | 3/2001 | Soykan et al. |
| 6,234,973 B1 | 5/2001 | Meador et al. |
| 6,236,889 B1 | 5/2001 | Soykan et al. |
| 6,237,398 B1 | 5/2001 | Porat et al. |
| 6,239,724 B1 | 5/2001 | Doron et al. |
| 6,248,080 B1 | 6/2001 | Miesel et al. |
| 6,253,260 B1 | 6/2001 | Beardsley et al. |
| 6,256,538 B1 | 7/2001 | Ekwall |
| 6,266,567 B1 | 7/2001 | Ishikawa et al. |
| 6,273,904 B1 | 8/2001 | Chen et al. |
| 6,277,078 B1 | 8/2001 | Porat et al. |
| 6,278,894 B1 | 8/2001 | Salo et al. |
| 6,287,332 B1 | 9/2001 | Bolz et al. |
| 6,305,381 B1 | 10/2001 | Weijand et al. |
| 6,308,099 B1 | 10/2001 | Fox et al. |
| 6,330,957 B1 | 12/2001 | Bell-Greenstreet |
| 6,331,163 B1 | 12/2001 | Kaplan |
| 6,347,245 B1 | 2/2002 | Lee et al. |
| 6,366,808 B1 | 4/2002 | Schroeppel et al. |
| 6,368,275 B1 | 4/2002 | Sliwa et al. |
| 6,397,661 B1 | 6/2002 | Grimes et al. |
| 6,409,674 B1 | 6/2002 | Brockway et al. |
| 6,409,675 B1 | 6/2002 | Turcott |
| 6,411,850 B1 | 6/2002 | Kay et al. |
| 6,416,474 B1 | 7/2002 | Penner et al. |
| 6,431,175 B1 | 8/2002 | Penner et al. |
| 6,432,050 B1 | 8/2002 | Porat et al. |
| 6,438,408 B1 | 8/2002 | Mulligan et al. |
| 6,441,747 B1 | 8/2002 | Khair et al. |
| 6,442,413 B1 | 8/2002 | Silver |
| 6,445,953 B1 | 9/2002 | Bulkes et al. |
| 6,456,883 B1 | 9/2002 | Torgerson et al. |
| 6,471,645 B1 | 10/2002 | Warkentin et al. |
| 6,472,991 B1 | 10/2002 | Schulman et al. |
| 6,475,170 B1 | 11/2002 | Doron et al. |
| 6,486,588 B2 | 11/2002 | Doron et al. |
| 6,504,286 B1 | 1/2003 | Porat et al. |
| 6,522,914 B1 | 2/2003 | Huvelle et al. |
| 6,526,314 B1 | 2/2003 | Eberle et al. |
| 6,567,700 B1 | 5/2003 | Turcott et al. |
| 6,574,510 B2 | 6/2003 | Von Arx et al. |
| 6,580,946 B2 | 6/2003 | Struble |
| 6,584,349 B1 | 6/2003 | Sage et al. |
| 6,584,354 B1 | 6/2003 | Mann et al. |
| 6,585,764 B2 | 7/2003 | Wright et al. |
| 6,589,187 B1 | 7/2003 | Dirnberger et al. |
| 6,599,242 B1 | 7/2003 | Splett et al. |
| 6,604,000 B2 | 8/2003 | Lu |
| 6,607,485 B2 | 8/2003 | Bardy |
| 6,609,023 B1 | 8/2003 | Fischell et al. |
| 6,615,083 B2 | 9/2003 | Kupper |
| 6,622,049 B2 | 9/2003 | Penner et al. |
| 6,622,050 B2 | 9/2003 | Thompson |
| 6,628,985 B2 | 9/2003 | Sweeney et al. |
| 6,628,989 B1 | 9/2003 | Penner et al. |
| 6,638,231 B2 | 10/2003 | Govari et al. |
| 6,644,322 B2 | 11/2003 | Webb |
| 6,650,939 B2 | 11/2003 | Taepke, II et al. |
| 6,654,638 B1 | 11/2003 | Sweeney |
| 6,660,034 B1 | 12/2003 | Mandrusov et al. |
| 6,675,049 B2 | 1/2004 | Thompson et al. |
| 6,682,985 B2 | 1/2004 | Yuzuriha et al. |
| 6,699,186 B1 | 3/2004 | Wolinsky et al. |
| 6,702,847 B2 | 3/2004 | DiCarlo |
| 6,708,061 B2 | 3/2004 | Salo et al. |
| 6,708,065 B2 | 3/2004 | Von Arx et al. |
| 6,712,772 B2 | 3/2004 | Cohen et al. |
| 6,719,689 B2 | 4/2004 | Munneke et al. |
| 6,720,709 B2 | 4/2004 | Porat et al. |
| 6,720,887 B1 | 4/2004 | Zunti |
| 6,733,447 B2 | 5/2004 | Lai et al. |
| 6,743,173 B2 | 6/2004 | Penner et al. |
| 6,754,795 B2 | 6/2004 | Chen et al. |
| 6,778,859 B2 | 8/2004 | Graindorge |
| 6,782,810 B2 | 8/2004 | Vilo |
| 6,783,499 B2 | 8/2004 | Schwartz |
| 6,792,308 B2 | 9/2004 | Corbucci |
| 6,792,311 B2 | 9/2004 | Fox et al. |
| 6,805,667 B2 | 10/2004 | Christopherson et al. |
| 6,809,507 B2 | 10/2004 | Morgan et al. |
| 6,823,210 B2 | 11/2004 | Eberle et al. |
| 6,824,512 B2 | 11/2004 | Warkentin et al. |
| 6,840,956 B1 | 1/2005 | Wolinsky et al. |
| 6,855,115 B2 | 2/2005 | Fonseca et al. |
| 6,859,665 B2 | 2/2005 | Ding et al. |
| 6,865,419 B2 | 3/2005 | Mulligan |
| 6,868,346 B2 | 3/2005 | Larson et al. |
| 6,869,404 B2 | 3/2005 | Schulhauser et al. |
| 6,871,088 B2 | 3/2005 | Chinchoy |
| 6,885,889 B2 | 4/2005 | Chinchoy |
| 6,895,265 B2 | 5/2005 | Silver |
| 6,907,285 B2 | 6/2005 | Denker et al. |
| 6,910,084 B2 | 6/2005 | Augustijn et al. |
| 6,915,162 B2 | 7/2005 | Noren et al. |
| 6,926,670 B2 | 8/2005 | Rich et al. |
| 6,937,900 B2 | 8/2005 | Pianca et al. |
| 6,949,075 B2 | 9/2005 | Hatlesad et al. |
| 6,961,448 B2 | 11/2005 | Nichols et al. |
| 6,961,617 B1 | 11/2005 | Snell |
| 6,970,742 B2 | 11/2005 | Mann et al. |
| 6,978,182 B2 | 12/2005 | Mazar et al. |
| 7,003,350 B2 | 2/2006 | Denker et al. |
| 7,016,721 B2 | 3/2006 | Lee et al. |

| | | |
|---|---|---|
| 7,018,336 B2 | 3/2006 | Enegren et al. |
| 7,027,872 B2 | 4/2006 | Thompson |
| 7,033,322 B2 | 4/2006 | Silver |
| 7,035,684 B2 | 4/2006 | Lee |
| 7,047,065 B2 | 5/2006 | Kalgren et al. |
| 7,061,381 B2 | 6/2006 | Forcier et al. |
| 7,088,254 B2 | 8/2006 | Liebenow |
| 7,127,290 B2 | 10/2006 | Girouard et al. |
| 7,130,678 B2 | 10/2006 | Ritscher et al. |
| 7,134,999 B2 | 11/2006 | Brauker et al. |
| 7,136,703 B1 | 11/2006 | Cappa et al. |
| 7,160,252 B2 | 1/2007 | Cho et al. |
| 7,198,603 B2 | 4/2007 | Penner et al. |
| 7,200,439 B2 | 4/2007 | Zdeblick et al. |
| 7,204,798 B2 | 4/2007 | Zdeblick et al. |
| 7,212,861 B1 | 5/2007 | Park et al |
| 7,214,189 B2 | 5/2007 | Zdeblick |
| 7,225,030 B2 | 5/2007 | Kroll et al. |
| 7,248,923 B2 | 7/2007 | Maile et al. |
| 7,294,105 B1 | 11/2007 | Islam |
| 7,335,161 B2 | 2/2008 | Von Arx et al. |
| 7,392,090 B2 | 6/2008 | Sweeney et al. |
| 7,399,313 B2 | 7/2008 | Brown et al. |
| 7,425,200 B2 | 9/2008 | Brockway et al. |
| 7,452,334 B2 | 11/2008 | Gianchandani et al. |
| 7,481,771 B2 | 1/2009 | Fonseca et al. |
| 2002/0023123 A1 | 2/2002 | Madison |
| 2002/0042561 A1 | 4/2002 | Schulman et al. |
| 2002/0045804 A1* | 4/2002 | Christopherson et al. .... 600/300 |
| 2002/0045812 A1 | 4/2002 | Ben-Haim et al. |
| 2002/0045836 A1 | 4/2002 | Alkawwas |
| 2002/0045921 A1 | 4/2002 | Wolinsky et al. |
| 2002/0077673 A1 | 6/2002 | Penner et al. |
| 2002/0123672 A1 | 9/2002 | Christophersom |
| 2002/0147388 A1 | 10/2002 | Mass et al. |
| 2002/0147406 A1 | 10/2002 | von Segesser |
| 2002/0151770 A1 | 10/2002 | Noll, III et al. |
| 2002/0177782 A1 | 11/2002 | Penner |
| 2002/0183628 A1 | 12/2002 | Reich et al. |
| 2002/0188323 A1 | 12/2002 | Penner et al. |
| 2003/0009204 A1 | 1/2003 | Amundson et al. |
| 2003/0114897 A1 | 6/2003 | Von Arx et al. |
| 2003/0114898 A1 | 6/2003 | Von Arx et al. |
| 2003/0130708 A1 | 7/2003 | Von Arx et al. |
| 2003/0136417 A1 | 7/2003 | Fonseca et al. |
| 2003/0149459 A1 | 8/2003 | Von Arx et al. |
| 2003/0158584 A1 | 8/2003 | Cates et al. |
| 2003/0181794 A1 | 9/2003 | Rini et al. |
| 2003/0191383 A1 | 10/2003 | Ben-Haim et al. |
| 2003/0199939 A1 | 10/2003 | Schmitt et al. |
| 2004/0032187 A1 | 2/2004 | Penner et al. |
| 2004/0044393 A1 | 3/2004 | Yarden et al. |
| 2004/0064133 A1 | 4/2004 | Miller et al. |
| 2004/0077937 A1 | 4/2004 | Yarden |
| 2004/0106874 A1 | 6/2004 | Eigler et al. |
| 2004/0122484 A1 | 6/2004 | Hatlestad et al. |
| 2004/0122486 A1* | 6/2004 | Stahmann et al. ............... 607/60 |
| 2004/0152999 A1 | 8/2004 | Cohen et al. |
| 2004/0172081 A1 | 9/2004 | Wang |
| 2004/0230225 A1 | 11/2004 | Penner et al. |
| 2005/0056539 A1 | 3/2005 | Morgan et al. |
| 2005/0060186 A1 | 3/2005 | Blowers et al. |
| 2005/0065815 A1 | 3/2005 | Mazar et al. |
| 2005/0102002 A1 | 5/2005 | Salo et al. |
| 2005/0137490 A1 | 6/2005 | Scheiner et al. |
| 2005/0149143 A1 | 7/2005 | Libbus et al. |
| 2005/0154321 A1 | 7/2005 | Wolinsky et al. |
| 2005/0159789 A1 | 7/2005 | Brockway et al. |
| 2005/0182330 A1 | 8/2005 | Brockway et al. |
| 2005/0187482 A1 | 8/2005 | O'Brien et al. |
| 2005/0192637 A1 | 9/2005 | Girouard et al. |
| 2005/0192844 A1 | 9/2005 | Esler et al. |
| 2005/0197585 A1 | 9/2005 | Brockway et al. |
| 2005/0215887 A1 | 9/2005 | Ben-Haim et al. |
| 2005/0222631 A1 | 10/2005 | Dalal et al. |
| 2005/0231374 A1 | 10/2005 | Diem et al. |
| 2005/0242479 A1 | 11/2005 | Petisce et al. |
| 2005/0288727 A1 | 12/2005 | Penner |
| 2006/0031378 A1 | 2/2006 | Vallapureddy et al. |
| 2006/0064133 A1 | 3/2006 | Von Arx et al. |
| 2006/0064134 A1 | 3/2006 | Mazar et al. |
| 2006/0064142 A1 | 3/2006 | Chavan et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0089694 A1 | 4/2006 | Zhang et al. |
| 2006/0136004 A1 | 6/2006 | Cowan et al. |
| 2006/0142651 A1 | 6/2006 | Brister et al. |
| 2007/0043394 A1 | 2/2007 | Zhang et al. |
| 2007/0049977 A1 | 3/2007 | Von Arx et al. |
| 2007/0060959 A1 | 3/2007 | Salo et al. |
| 2007/0129765 A1 | 6/2007 | Gilkerson et al. |
| 2007/0142727 A1 | 6/2007 | Zhang et al. |
| 2008/0015421 A1 | 1/2008 | Penner |
| 2008/0021333 A1 | 1/2008 | Huelskamp |
| 2008/0021972 A1 | 1/2008 | Huelskamp et al. |
| 2008/0058651 A1 | 3/2008 | Shen et al. |
| 2008/0071178 A1 | 3/2008 | Greenland et al. |
| 2008/0077440 A1 | 3/2008 | Doron |
| 2008/0312553 A1 | 12/2008 | Timmons |

FOREIGN PATENT DOCUMENTS

| | | |
|---|---|---|
| EP | 0897690 | 2/1999 |
| EP | 1266606 | 12/2002 |
| EP | 1169085 | 8/2004 |
| JP | 2002/224053 | 8/2002 |
| WO | WO 83/03345 | 10/1983 |
| WO | WO97/01986 | 1/1997 |
| WO | WO97/32519 | 9/1997 |
| WO | WO97/33513 | 9/1997 |
| WO | WO97/47236 | 12/1997 |
| WO | WO98/26716 | 6/1998 |
| WO | WO98/29030 | 7/1998 |
| WO | WO99/17095 | 4/1999 |
| WO | WO99/26530 | 6/1999 |
| WO | WO99/34453 | 7/1999 |
| WO | 9947205 | 9/1999 |
| WO | WO99/55223 | 11/1999 |
| WO | WO99/55225 | 11/1999 |
| WO | WO99/59460 | 11/1999 |
| WO | WO99/66988 | 12/1999 |
| WO | WO00/16686 | 3/2000 |
| WO | WO 00/47109 | 8/2000 |
| WO | WO00/58744 | 10/2000 |
| WO | WO01/28627 | 4/2001 |
| WO | WO0156467 | 8/2001 |
| WO | WO01/74278 | 10/2001 |
| WO | WO02/03347 | 1/2002 |
| WO | WO02/32502 | 4/2002 |
| WO | WO 03/002243 | 1/2003 |
| WO | WO 03/096889 | 11/2003 |
| WO | WO 2004/056301 | 7/2004 |
| WO | WO 2004/060043 | 7/2004 |
| WO | WO2005/118056 | 12/2005 |
| WO | WO2006/045073 | 4/2006 |
| WO | WO2006/045074 | 4/2006 |
| WO | WO2006/045075 | 4/2006 |
| WO | WO2006/069215 | 6/2006 |
| WO | WO2007/030474 | 3/2007 |
| WO | WO2007/047287 | 4/2007 |
| WO | WO2008/011592 | 1/2008 |
| WO | WO2008/011593 | 1/2008 |
| WO | WO2008/154145 | 12/2008 |

OTHER PUBLICATIONS

International Search Report and Written Opinion for PCT/US2005/033460, filed Sep. 15, 2005, both mailed Feb. 8, 2006.

International Search Report and Written Opinion for PCT/US2006/061926, filed Dec. 12, 2006, both mailed Jun. 7, 2007.

Office Action received for U.S. Appl. No. 10/943,269, mailed Oct. 6, 2006.

Office Action received for U.S. Appl. No. 10/943,271, mailed Oct. 6, 2006.

Office Action received for U.S. Appl. No. 10/943,626, mailed Apr. 27, 2007.

U.S. Appl. No. 10/943,626, filed Sep. 17, 2004.

U.S. Appl. No. 11/300,769, filed Dec. 15, 2005.

B. C. Penney et al., "Simplified electrode array for impedance cardiography," Medical & Biological Engineering & Computing, 1985, 23, p. 1-7.

B. Henderson et al., "Interaction of Photodynamic Therapy and Hyperthermia: Tumor Response and Cell Survival after Treatment of Mice in Vivo," Cancer Research, vol. 45, 6071 (Dec. 1985).

Bennett et al., "Subcutaneous pressure measurement as a surrogate for an external pressure reference for chronic implantable pressure monitoring," Journal of Cardial Failure, Churchill Livingstone, vol. 9, No. 5, p. S51, Oct. 1, 2003, abstract only.

Bonnefoy E, Ninet J, Robin J, Leroux F, Boissonat P, Brule P, Champsaur G., 1994, Bipolar intramyocardial electrogram from an implanted telemetric pacemaker for the diagnosis of cardiac allograft rejection, Pacing Clin Electrophysiol, 17(11 Pt 2):2052-6.

C. Hierold et al. (Germany, 1998) "Implantable Low Power Integrated Pressure Sensor System for Minimal Invasive Telemetric Patient Monitoring" IEEE, pp. 568-573.

Dipl.-Ing. Torsten Eggers et al. (Germany) "Implantable Telemetric Endosytem (ITES)" IMSAS Institut Fur Mikrosensoren-Aktuatoren Und-Systeme, 1998. 2 pp.

E R. Cosman et al. (Massachussetts, Apr. 1979) "A Telemetric Pressure Sensor for Ventricular Shunt Systems" Surgical Neurology vol. 11, No. 4, pp. 287-294.

G.W.H. Schurink et al. (1998) "Late Endoleak After Endovascular Therapy for Abdominal Aortic Aneurysm" Eur. J. Vasc. Endovasc. Surg. vol. 17, pp. 448-450.

Gerhausser A, Reichel T, Neukomm P A, Bolz A, Hugel J, Schaldach M, 1997, Diagnosis of rejection after kidney transplantation by impedance spectroscopy with an implantable measuring system, Biomed Tech (Berl), 42 Suppl. 160-1.

GH White et al. (1997) "Endoleak Following Endoluminal Repair of AAA: Management Options and Patient Outcomes", J. Endovasc Surg, pp. 1-45.

Graichen et al., "Patient Monitoring System for Load Measurement with Spinal Fixation Devices," Med. Eng. Phys. 18, (1996), pp. 167-174.

Haas et al., "Photodynamic Effects of Dyes on Bacteria," Published in Mutation Research, 1979, vol. 60, pp. 1-11.

Hashima et al., "Nonhomogenous Analysis of Epicardial Strain Distributions During Acute Myocardial Ischemia in the Dog," J Biomech 1993, Jan. 26: 19-35.

Hetzer R. et al., 1998, Daily non-invasive rejection monitoring improves long-term survival in pediatric heart transplantation, Ann. Thorac. Surg. (66):1343-1349.

J.A. Parrish, "Photobiologic Consideration on Photoradiation Therapy," pp. 91-108, Porphyrin Photosensitization, Plenum Press, (1983).

K.E. Uhrich et al., "Synthesis and characterization of degradable poly(anhydride-co-imides)", Macromolecules, 1995, 28, 2184-93.

Karl E. Richard et al. (Germany, Jan. 1999) "First clinical results with a telemetric shunt-integrated ICP-sensor" Neurological Research vol. 21, pp. 117-120.

Labrousse and Satre, "Photodynamic Killing of Dictyostelium Discoideum Amoebae Mediated by 4',5'-Diiodofluorescin Isothiocyanate Dextran. A strategy for the isolation of Thermoconditional Endocytosis Mutants," published in Photochemistry and Photobiology.

Mackay et al., "Bio-medical Telemetry: Sensing and Transmitting Biological Information from Animals and Man," John Wiley & Sons, Inc. New York (1970) pp. 244-245.

Pfitzmann R, Muller J, Grauhan O. Cohnert T, Hetzer R, Z Kardiol, 1998, Measuring bioelectric myocardial impedance as a non invasive method for diagnosis of graft rejection after heart transplantation, 87(4):258-266.

Pirolo J S, Shuman T S, Brunt E M, Liptay M J, Cox J L, Ferguson T B Jr., J Thoracic Cardiovasc Surg, 1992, Noninvasive detection of cardiac allograft rejection by prospective telemetric monitoring, 103(5):969-79.

Prof. Dr. Johannes Zacheja et al. (Germany, Sep. 1996) "An Implantable Microsystem for Biomedical Applications" Micro System Technologies 96, pp. 717-722.

S.K. Gupta et al. (1999) "Use of a Piezoelectric Film Sensor for Monitoring Vascular Grafts", The American Journal of Surgery, vol. 160, pp. 182-186.

T. Chuter et al. (Sweden, Jan. 1997) "Aneurysm Pressure Following Endovascular Exclusion" Eur. J. Vasc. Endovasc. Surg. vol. 13, pp. 85-87.

Z. Tang et al. (May 1995) "Data Transmission from an Implantable Biotelemeter by Load-Shift Keying Using Circuit Configuration Modulator" IEEE Transactions on Biomedical Engineering. vol. 42, No. 5, pp. 524-528.

Extended European Search Report issued in EP 10184174, mailed Dec. 7, 2010.

* cited by examiner

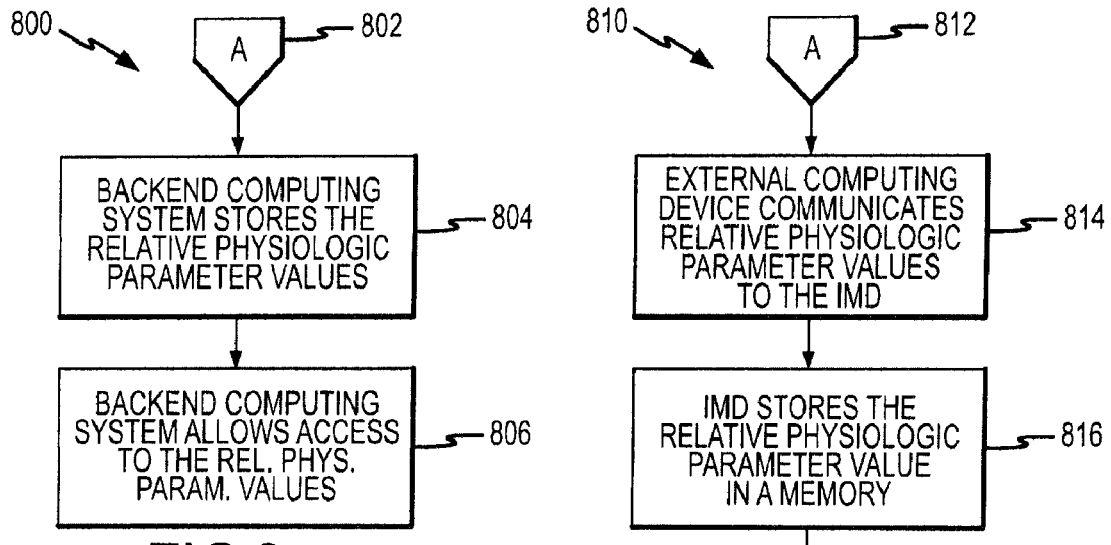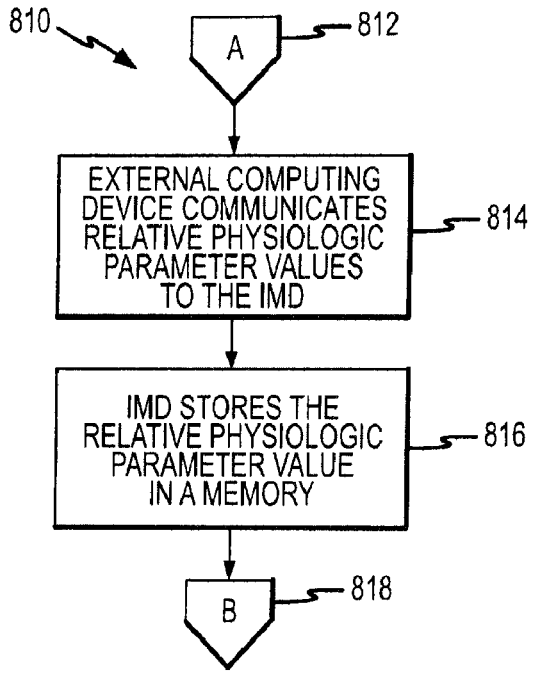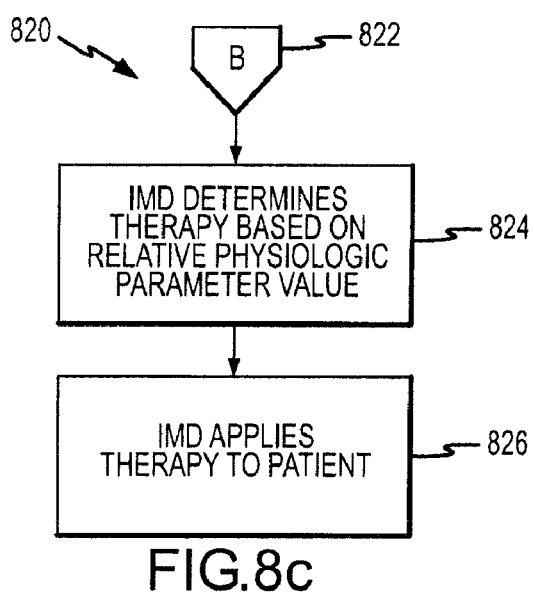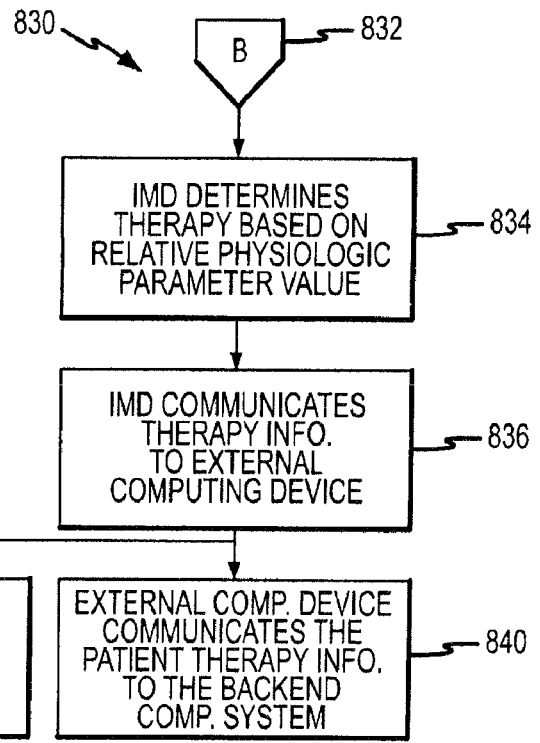

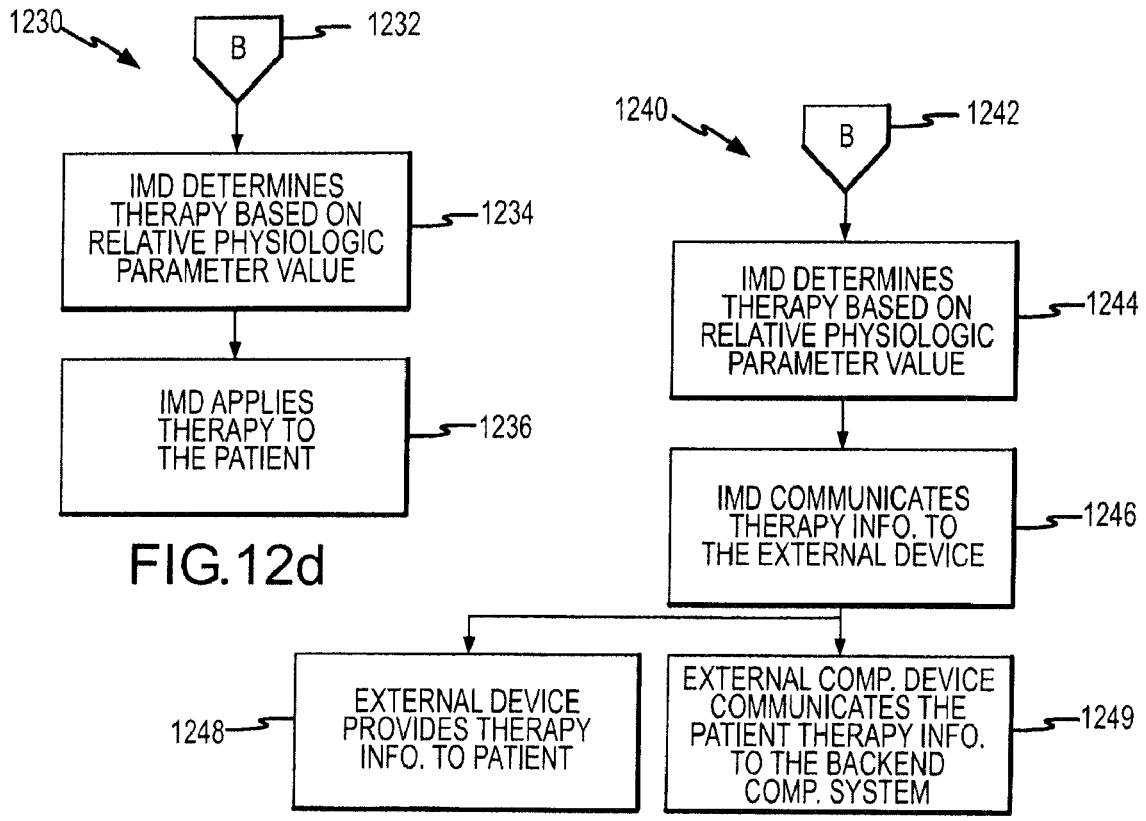
FIG.12d
FIG.12e
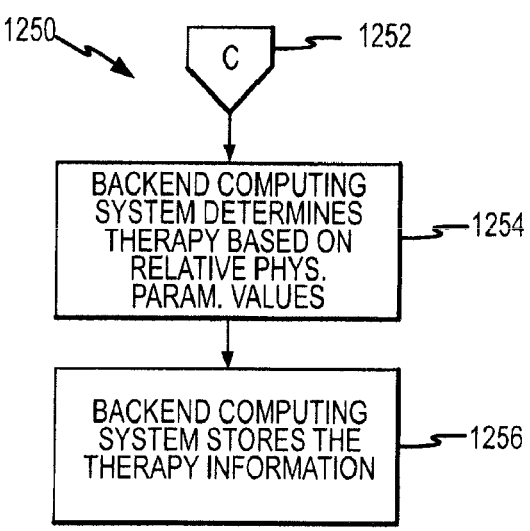
FIG.12f

SYSTEMS AND METHODS FOR DERIVING RELATIVE PHYSIOLOGIC MEASUREMENTS USING A BACKEND COMPUTING SYSTEM

CROSS-REFERENCE TO RELATED APPLICATIONS

The present application is related to three co-pending patent applications: U.S. patent application Ser. No. 10/943,626, filed on Sep. 17, 2004, entitled "SYSTEMS AND METHODS FOR DERIVING RELATIVE PHYSIOLOGIC MEASUREMENTS," and filed by Mazar et al.; U.S. patent application Ser. No. 10/943,269, filed on Sep. 17, 2004, entitled "SYSTEMS AND METHODS FOR DERIVING RELATIVE PHYSIOLOGIC MEASUREMENTS USING AN EXTERNAL COMPUTING DEVICE," and filed by Von Arx et al.; and U.S. patent application Ser. No. 10/943,271, filed on Sep. 17, 2004, entitled "SYSTEMS AND METHODS FOR DERIVING RELATIVE PHYSIOLOGIC MEASUREMENTS USING AN IMPLANTED SENSOR DEVICE," and filed by Chavan et al. Each of the above-identified applications is filed on the same date as the present application, and each of the above-identified applications is incorporated by reference herein for all purposes.

BACKGROUND OF THE INVENTION

The present invention relates generally to measuring physiologic parameters of a patient, and more particularly, to systems, methods and devices for measuring and deriving physiologic parameters relative to various environmental parameters.

Medical devices are known that can be implanted within a patient's body for monitoring one or more physiological parameters and/or to provide therapeutic functions. For example, sensors or transducers can be placed in the body for monitoring a variety of properties, such as temperature, blood pressure, strain, fluid flow, chemical properties, electrical properties, magnetic properties, and the like. In addition, medical devices can be implanted that perform one or more therapeutic functions, such as drug delivery, cardiac pacing, defibrillation, electrical stimulation, and the like.

In many cases, the implanted medical devices ("IMDs") are configured or adapted to communicate with external controllers or programmers, for example, to communicate data between the IMD and the external programmers, and/or to activate or otherwise control the IMDs. Typically, the IMDs can communicate with the external programmers via a wireless communication link, such as an RF communication link, or the like.

As mentioned above, IMDs can be configured to measure or sense a number of different parameters in the body. One parameter of particular interest is blood pressure. The implantable biosensors that measure pressure deep within anatomical structures, however, typically can only communicate the absolute pressure associated with the immediate anatomical environment. These devices are not capable of communicating gauge pressure because they are confined and sealed away from the ambient pressure external the body. In most cases, it is gauge pressure and not absolute pressure that is sought to be known, since the body regulates its activities based on the ambient pressure. Gauge pressure may be determined by correlating the absolute pressure with the ambient pressure. Similar situations exist for other parameters, as well, such as temperature.

Thus, a need exists for systems, methods, and/or devices for adjusting measured physiologic parameters, such as pressure, temperature and others, based on ambient or other environmental conditions.

BRIEF SUMMARY OF THE INVENTION

One embodiment of the present invention relates to a system for deriving physiologic measurement values that are relative to ambient conditions. In one embodiment, the system comprises an implantable medical device ("IMD"), an external computing device, and a backend computing system. The IMD determines an absolute physiologic parameter value within a patient's body, and communicates the absolute physiologic parameter value outside the patient's body, for example, to the external computing device. Further, the external computing device receives the absolute physiologic parameter from the IMD and communicates it to the backend computing system. The backend computing system receives the absolute physiologic parameter value and obtains an ambient condition value outside the body that can affect the absolute physiologic parameter value. The backend computing system then calculates a relative physiologic parameter value from the ambient condition value and the absolute physiologic parameter value, and in some embodiments, stores the relative physiologic parameter value in a storage location, such as a memory or database.

In one embodiment, the absolute physiologic parameter value and/or the ambient condition value can be marked with a time stamp. Thus, because time stamps are used, the backend computing system can select an ambient condition value that is obtained or measured at a time reasonably close to the time when the absolute physiologic parameter value is measured to calculate the relative physiologic parameter value.

Further, in another embodiment, the backend computing system can communicate the relative physiologic parameter value to the external computing device, which also can communicate the relative physiologic parameter value to the IMD. The IMD then can receive the relative physiologic parameter value and store it in a memory.

In some embodiments, the backend computing system can be a database accessible by one or more health care providers. Thus, the one or more health care providers can obtain the relative physiologic parameter value from the database and use the relative physiologic parameter value to provide a service to the patient, such as diagnosing the patient, prescribing medication to the patient, providing a therapy to the patient, modifying one or more settings of the IMD, or the like.

In accordance with one embodiment, the absolute physiologic parameter value comprises blood pressure (e.g., intravascular or intracardiac blood pressure). Thus, in accordance with this embodiment, the ambient condition value comprises an ambient pressure value, and the relative physiologic parameter value comprises blood pressure relative to the ambient pressure. For example, the relative physiologic parameter value can be a gauge pressure value calculated by subtracting the ambient pressure value from the blood pressure.

In yet another embodiment, the blood pressure can be determined by measuring the blood pressure with a pressure sensor and adjusting the blood pressure with a sensor specific adjustment factor to obtain an absolute blood pressure value.

In addition, in other embodiment, the external computing device can include a sensor for measuring the ambient condition value. In this embodiment, the external computing device communicates the ambient condition value to the backend computing system. Further, in other embodiments, backend computing system can receive the ambient condition value from an ambient condition source, such as an external monitor or other source. If an external monitor is used to obtain the ambient condition value, it can communicate the ambient condition value to the external computing device, which communicates the ambient condition value to the backend computing system. In some embodiments, the external monitor can be a wireless communication device carried on or near the patient's body. For example, the external monitor can be a device adapted to be worn around a patient's body part, a device that can be connected to a belt, a device that can be worn as a patch, a personal digital assistant (PDA), a device that can be carried in a pocket or a personal carry bag, a customized cell phone or pager, or any other suitable device that can perform the functions of the external monitor.

In some embodiment, the external computing device can be an IMD programmer, or a repeater device in communication with the backend computing system. In addition, in some embodiments, the IMD and the external computing device can communicate via a wireless communication connection, such as, for example, a radio frequency communication connection, an acoustic communication connection, a magnetic field communication connection, an optical communication connection, or any other suitable wireless communication connection.

The IMD can be any suitable implantable medical device. For example, in some embodiments, the IMD can be a physiologic parameter sensor, a pacemaker, a defibrillator, a bi-ventricular pacer, a ventricular assist blood pump, a drug delivery pump, a drug infusion device, a neurostimulating device, an intra-ocular shunt, an intra-cranial shunt, or any other suitable IMD. Also, the IMD can be adapted to provide therapy to a patient. In accordance with this embodiment, the IMD can be configured to use the relative physiologic parameter value to determine the proper therapy to provide to the patient. For example, in some embodiments, the IMD can use the relative physiologic parameter value to determine and provide therapies, such as, cardiac pacing therapy, anti-tachycardia therapy, drug delivery therapy, neurostimulation therapy, blood pump therapy, or any other suitable therapy provided by IMDs.

In still other embodiments, the IMD can include a processor that can be adapted to generate patient therapy information based at least in part on the relative physiologic parameter value. In accordance with this embodiment, the implantable medical device can be configured to communicate the patient therapy information to the external computing device, and the external computing device can include a patient communication interface adapted to provide the patient therapy information to the patient. In other embodiments, the external computing device can communicate the patient therapy information to the backend computing system for access by one or more health care providers.

In yet another embodiment, the backend computing system can determine a proper therapy to provide to a patient. In the embodiment, the backend computing system can use the relative physiologic parameter value to determine the therapy, and it can store the therapy information for access by one or more health care providers.

In yet other embodiments, the present invention can include methods performed by the IMD, the external computing device, and/or the backend computing system, and the present invention can include the IMDs and/or the external computing devices individually.

A more complete understanding of the present invention may be derived by referring to the detailed description of preferred embodiments and claims when considered in connection with the figures.

BRIEF DESCRIPTION OF THE DRAWINGS

In the Figures, similar components and/or features may have the same reference label. Further, various components of the same type may be distinguished by following the reference label with a second label that distinguishes among the similar components. If only the first reference label is used in the specification, the description is applicable to any one of the similar components having the same first reference label irrespective of the second reference label.

FIGS. 5-12 are flow charts illustrating various embodiments of methods of the present invention.

DETAILED DESCRIPTION OF THE INVENTION

The present invention relates generally to measuring physiological parameters of a patient, and more particularly, to systems, methods and devices for measuring and deriving physiological parameters relative to various environmental parameters. In contrast to prior art systems and methods, the present invention utilizes a backend computing system to obtain ambient measurement values, and then the backend computing system use the ambient values along with the measured physiologic parameters to calculate relative physiologic parameter values.

As discussed herein, the present invention relates to systems and methods for obtaining relative physiologic parameter values. The physiologic parameter values obtained can be any physiologic measurement, such as, blood pressure, temperature, blood or fluid flow, strain, electrical, chemical or magnetic properties within the body, or the like. As one skilled in the art will appreciate, the type of measurement being taken may determine whether the measurement will need to be adjusted for ambient or other environmental conditions that may affect the measurements within the body. For example, it is known that ambient pressure will affect intravascular blood pressure. Further, outside temperature may affect the internal body temperature of a person or other animal, depending, in part, on the severity of the outside temperature. Also, other environmental conditions, such as, altitude, humidity, electric or magnetic fields, or chemical compositions may affect other physiologic measurements of interest. Accordingly, the present invention can be used to adjust any internal physiologic measurements relative to environmental conditions, and thus, is not limited in scope to any particular measurement. Of course, as one skilled in the art will appreciate, adjusting measured internal blood pressure relative to ambient pressure (which also can be derived from or affected by temperature, humidity, altitude, etc.) is of particular interest for many clinical and therapeutic applications, and the present invention is well suited to obtain relative pressure values.

Figure 1:
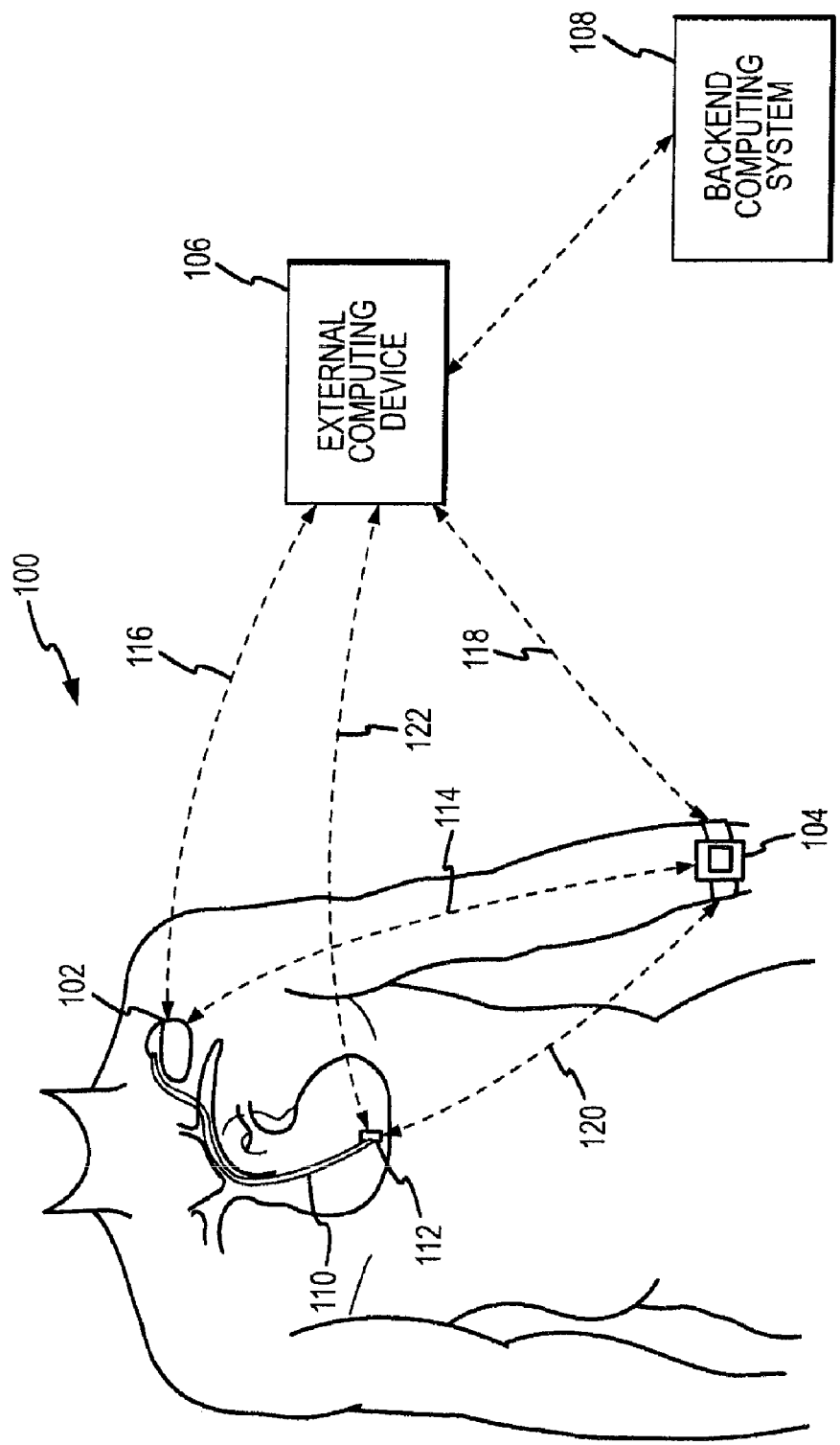
FIG. 1 is a diagram showing one embodiment of a system of the present invention.

Referring now to FIG. 1, one embodiment of a system 100 for deriving relative physiologic measurement values is shown. In accordance with the illustrated embodiment, system 100 includes an implantable medical device ("IMD") 102, an external monitoring device 104, an external computing device 106, and a backend computing system 108.

IMD 102 can be any type of implantable medical device that is configured to obtain physiologic measurements of a patient and/or provide therapy to the patient. For example, IMD 102 can be a pacemaker, an implantable cardioverter defibrillator ("ICD"), a cardiac resynchronization device, a bi-ventricular pacer, a ventricular assist blood pump, a drug delivery pump, a drug infusion device, a neurostimulating device, an intra-ocular shunt, an intra-cranial shunt, or any other suitable implantable device, which can obtain or measure physiologic parameter values. In the embodiment illustrated in FIG. 1, IMD 102 is a cardiac device, such as a pacemaker or ICD, which has one or more leads 110 that can include sensors or sensor circuitry 112 for obtaining physiologic measurements (e.g., blood pressure or the like) and therapy delivery systems (also 112) for providing cardiac therapy to the patient.

In addition, in alternative embodiments, sensors and/or therapy delivery systems 112 can be located separate from leads 110, and the sensor data can be transmitted to IMD 102 via other communication medium, such as a coupled communication connection, or a wireless communication connection. If a wireless communication connection is used, the wireless connection can be a radio frequency (RF) connection, an acoustic connection (e.g., ultrasound), an optical connection, an electric field connection, or any other suitable communication connection. For example, in one embodiment, sensors and/or therapy delivery systems 112 can be configured in one or more satellite devices (e.g., chronically implanted stent devices) as is disclosed in Published U.S. patent application No. 2003/0158584 A1, published on Aug. 21, 2003, and entitled "Chronically-Implanted Device For Sensing and Therapy," the entirely of which is incorporated by reference herein for all purposes.

In addition, in some embodiments, IMD 102 is operable to communicate with external monitoring device 104 and external computing device 106 via wireless connections 114 and 116, respectively. Similarly, in some embodiments, external monitoring device 104 is operable to communicate with external computing device 106 via wireless connection 118. Further, in other embodiments, external monitor 104 and external computing device 106 can be in wireless communication with sensor circuitry 112 via wireless connections 120 and 122, respectively. Each of these different embodiments will be discussed in more detail below. Wireless connections 114, 116, 118, 120 and 122 all can be uni-directional or bi-directional communication links, depending on the IMD and the data being transferred. As such, IMD 102 and/or sensor circuitry 112 can send information to and receive information from external monitoring device 104 and external computing device 106 via the communication connections. Similarly, external monitoring device 104 can communicate bi-directionally with external computing device 106.

Figure 2:
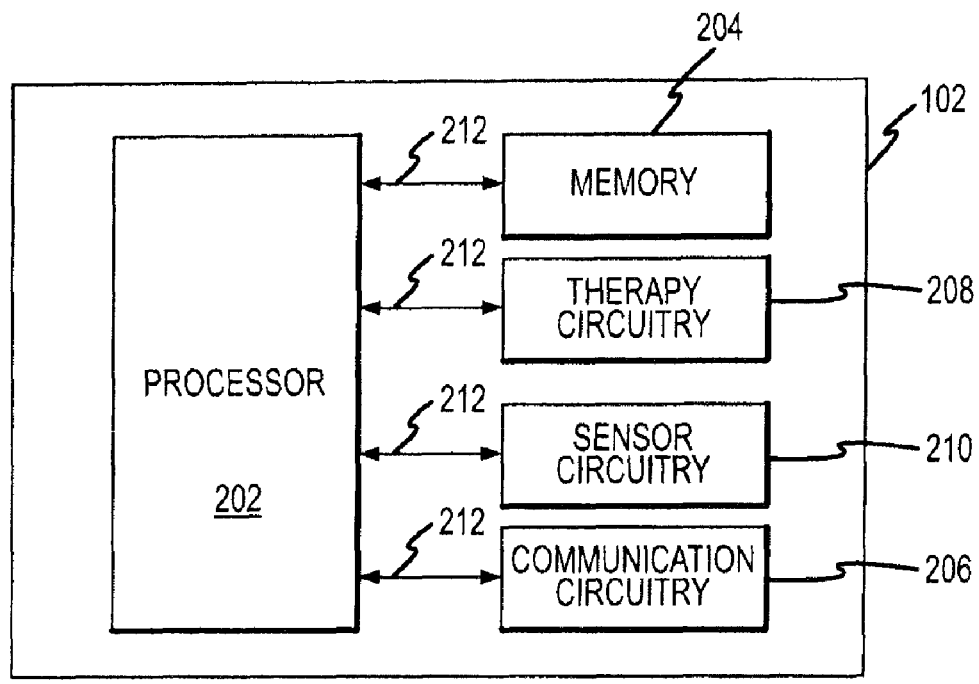
FIG. 2 is a block diagram showing one embodiment of an implantable medical device.

Referring now to FIG. 2, one embodiment of an IMD 102 is illustrated. In accordance with the illustrated embodiment, IMD 102 comprises a processor 202, a memory 204, communication circuitry 206, therapy circuitry 208 and sensor circuitry 210. Memory 204, communication circuitry 206, therapy circuitry 208 and sensor circuitry 210 all are in electrical communication with processor 202, as is illustrated by arrows 212.

As one skilled in the art will appreciate, processors and memory devices are well known in the art, and the specific type and/or style of processor or memory device that can be used in IMD 102 is not limited. Accordingly, processor 202 can be any suitable processing device currently known or hereinafter developed, and memory device 204 can be any suitable memory device currently known or hereinafter developed.

Communication circuitry 206 is circuitry that allows IMD 102 to communicate with other devices, such as external computing device 106, external monitoring device 104, other IMDs, or other external devices. As discussed above, IMD 102 communicates with other devices via a wireless connection. The wireless connection can be, for example, a near field radio frequency (RF) communication connection, a far field RF communication connection, an acoustic communication connection (e.g., an ultrasound connection), an optical communication connection, or any other suitable wireless communication connection.

In one embodiment, communication circuitry 206 can include circuitry for both near field RF telemetry and far field RF telemetry. For example, one embodiment of communication circuitry that can be used in IMD 102 is disclosed in Published U.S. patent App. No. U.S. 2003/0114897 A1, published on Jun. 19, 2003, and entitled "Implantable Medical Device with Two or More Telemetry Systems," and Published U.S. patent App. No. U.S. 2003/0114898 A1, published on Jun. 19, 2003, and entitled "Telemetry Duty Cycle Management System for an Implantable Medical Device," both of which are incorporated by reference herein for all purposes.

In addition, in other embodiments, power saving wireless communication circuitry and methods can be used. For example, the IMD communication circuitry 206 can be configured to reside in a power-saving, sleep mode for a majority of the time. In accordance with this embodiment, communication circuitry 206 can be configured to "wake-up" on a periodic basis to communicate with an external device. Upon "wake-up" the external device will monitor for RF activity, and if the external device locates it, communication between the IMD and the external device can be initiated. There are a number of different ways IMD power-saving modes can be implemented, and the present invention is not limited to any particular one. Indeed, the aforementioned Published U.S. patent App. Nos. U.S. 2003/0114897 A1 and U.S. 2003/0114898 A1 disclose different ways of implementing IMD power-saving modes, which, as discussed above, are incorporated herein by reference for all purposes. In addition, additional power management systems and methods are disclosed in Published U.S. patent App. No. U.S. 2003/0149459 A1, published on Aug. 7, 2003, and entitled "Methods and Apparatuses for Implantable Medical Device Telemetry Power Management," the entirety of which is incorporated by reference herein for all purposes.

Further, in accordance with other embodiments, communication circuitry 206 can be configured to communicate with an intermediary telemetry device, which, in turn, can facilitate communication with the external monitoring device 104 and/or external computing device 106. One example of this type of configuration is disclosed in Published U.S. patent App. No. U.S. 2003/0130708, published on Jul. 10, 2003, and entitled "Two-Hop Telemetry Interface for Medical Device," the entirety of which is incorporated by reference herein for all purposes. In addition, other configurations for RF telemetry are known, and communication circuitry 206 can embody those configurations, as well. Thus, as one skilled in the art will appreciate, communication circuitry 206 is not limited by any particular configuration or communication means.

Therapy circuitry 208 comprises circuitry for providing one or more therapeutic functions to a patient. For example, therapy circuitry 208 can include circuitry for providing heart pacing therapy, cardiac defibrillation therapy, cardiac resynchronization therapy, drug delivery therapy, or any other therapy associated with a suitable IMD. In the case of cardiac therapy (e.g., pacing, defibrillation, etc.), therapy circuitry 208 can include cardiac leads for delivering the therapy to particular locations in the heart. In other embodiments, the therapy circuitry and/or therapy delivery mechanisms can reside in a satellite device wirelessly coupled to the IMD body 102, as discussed below.

Finally, sensor circuitry 210 comprises the sensors and circuitry needed to obtain or measure the physiologic parameters. For example, to obtain a blood pressure (e.g., intravascular or intracardiac blood pressure), sensor circuitry 210 comprises one or more pressure sensors and associated circuitry for recording the pressure accurately. Pressure sensors and the associated circuitry are well known in the art, and therefore, will not be disclosed in detail herein. In addition, in other embodiments, sensor circuitry 210 can be configured to obtain other physiologic parameters, such as temperature, electrical impedance, position, strain, pH, fluid flow, blood oxygen levels, and the like. In these cases, sensor circuitry 210 will include suitable bio-sensors for obtaining the corresponding physiologic parameters.

Also, as one skilled in the art will appreciate, the sensors and/or sensor circuitry can be, and many times are, electrically coupled to IMD 102, but placed remotely from the IMD; e.g., at the end of a lead or in a satellite device in wireless communication with IMD 102. FIG. 1 illustrates an embodiment in which the sensors and/or therapy delivery mechanisms 112 are connected to IMD 102 via leads 110.

In an alternative embodiment, IMD 102 can comprise a planet/satellite configuration, in which the satellite portion of the IMD includes sensor and/or therapy delivery circuits and mechanisms. Such a configuration is disclosed in Published U.S. patent application No. U.S. 2003/0158584 A1, published on Aug. 21, 2003, and entitled "Chronically-Implanted Device for Sensing and Therapy," the entirety of which is incorporated herein by reference for all purposes. In this system, the planet or main body of the IMD communicates with one or more satellite sensor/therapy devices either by an electrical wire connection or wirelessly. In some embodiments, the planet or main body can command each satellite to provide sensing functions and therapy functions, such as delivering cardiac electrical pulses, drug delivery, or other functions, as discussed above. In other embodiments, the satellite devices can function autonomously, and then communicate with the planet device at their own direction, at the planet's direction, or at timed intervals. The relationships between the planet device and the satellite device(s) are discussed in more detail in the incorporated reference.

Figure 3:
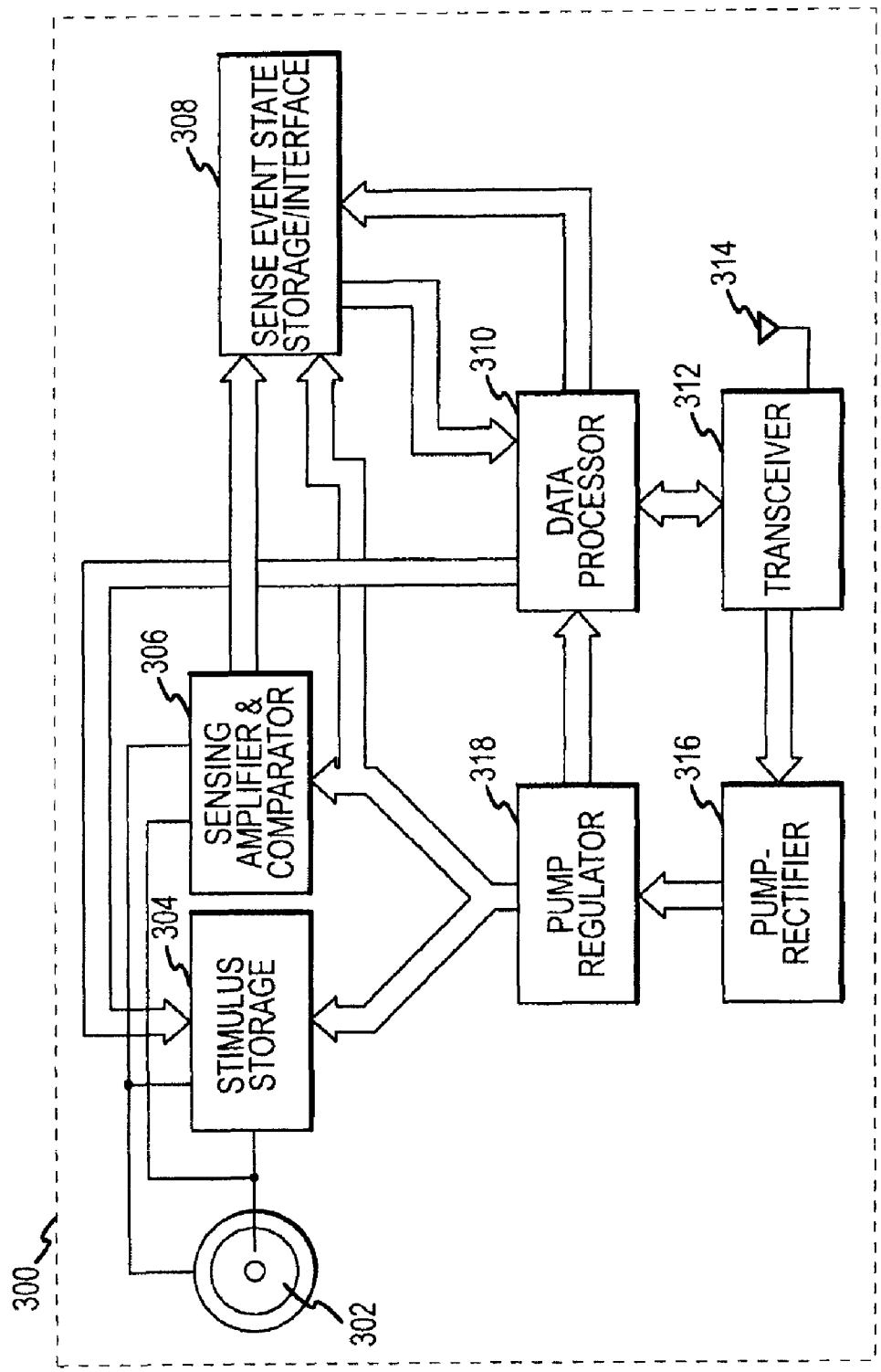
FIG. 3 is a block diagram showing one embodiment of a remote sensor system of an implantable medical device.

In accordance with one embodiment of the invention, the satellite sensor/therapy devices can be configured as stent-like, intraveous, chronically-implanted devices. The configuration of embodiments of stent-like devices is disclosed in more detail in the incorporated Published U.S. patent application No. U.S. 2003/0158584. FIG. 3, however, illustrates one embodiment of sensing and/or therapy circuitry 300 of a satellite device. In accordance with the illustrated embodiment, the circuitry 300 comprises a pair of electrodes 302, a stimulus storage unit 304, a sensing amplifier and comparator logic 306, a sense event state storage and interface 308, a data processor 310, a transceiver 312, an antenna 314, a pump-rectifier 316, and a pump-regulator 318. According to various embodiments, the satellite is designed for mechanical, electrical and/or chemical sensing, and for mechanical, electrical and/or drug-eluting therapies.

The operation of circuitry 300 is described in greater detail in the incorporated Published U.S. patent application No. U.S. 2003/0158584. However, in accordance with one embodiment, antenna 314 and transceiver 312 can be configured to communicate with the planet or main body of the IMD 102, with external monitor 104, or with external computing device 106. Such communication connections can be RF connections, acoustic connections (e.g., ultrasound), optical connections, or other suitable communication connections. In addition, antenna 314 and transceiver 312 can be configured to communicate with the multiple devices using one or more different connection types.

As discussed in more detail below, in some embodiments, sensor/therapy circuitry 300 is operable to receive ambient condition values, for example, from the main body of the IMD 102, external monitor 104 or external computing device 106 and calculate a relative physiologic parameter value using the ambient condition value. In accordance with these embodiments of the invention, data processor 310 can be configured to calculate the relative physiologic parameter values using measured values and the received ambient condition values. In addition, data processor 310 is operable to format data received by circuitry 300, as well as format data being transmitted by the satellite device. Again, a more complete description of the operation and configuration of the satellite device and associated circuitry is set forth in the incorporated reference.

Referring again to FIG. 1, external monitoring device 104 comprises a device that is adapted to obtain an ambient condition value or other environmental condition value outside the body that can affect the measured physiologic parameter value, and then, in some embodiments, calculate a relative physiologic parameter value using the measured physiologic parameter value and the ambient condition value. For example, as discussed in more detail below, when determining intravascular blood pressure, external monitoring device 104 can calculate a gauge blood pressure by adjusting the measured blood pressure value with an atmospheric or barometric pressure value.

External monitoring device 104 can comprise any type of processor-based device that can be carried on or near a patient's body. For example, external monitoring device 104 can be a device that is adapted to worn around a part of a patient's body, such as a wrist watch, a device connected to a belt, or some other device adapted to be worn around an ankle, leg, arm, neck, chest, stomach, etc. In addition, in other embodiments, external monitoring device can be a computing device worn as a patch, or a computing device that can be carried in a pocket, on a belt clip, or in a personal carry bag, such as a PDA, or a customized cellular phone or pager. One skilled in the art will appreciate that other device can be used as well.

Figure 4:
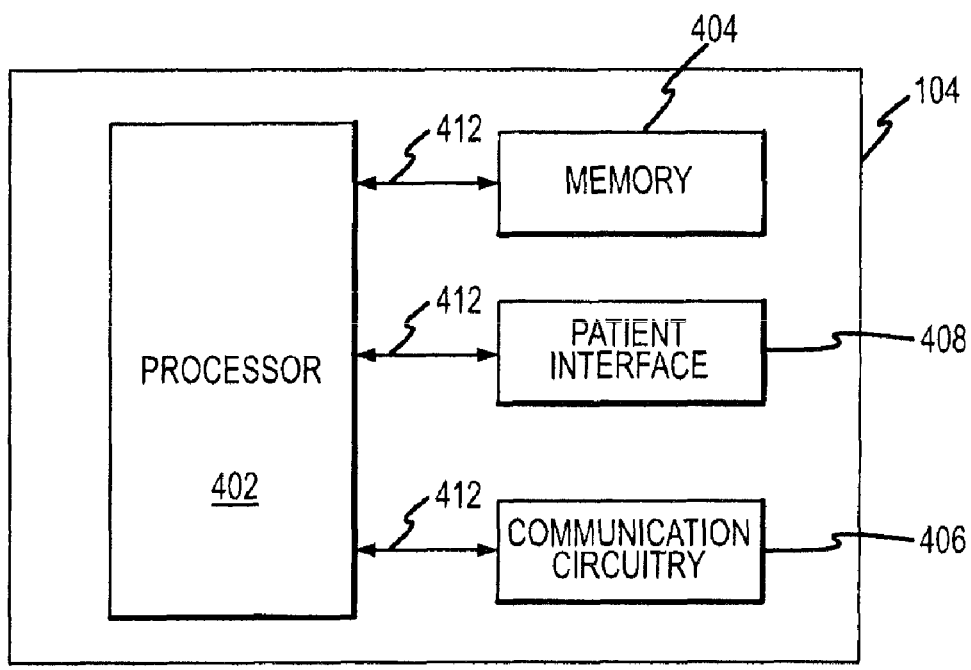
FIG. 4 is a block diagram of one embodiment of an external monitor.

Referring now to FIG. 4, one embodiment of an external monitoring device 104 is shown. In the illustrated embodiment, external monitoring device 104 comprises a processor 402, a memory 404, communication circuitry 406 and a patient interface 408. Memory 404, communication circuitry 406, and patient interface 408 all are in electrical communication with processor 402, as is illustrated by arrows 412.

As one skilled in the art will appreciate, and as discussed above with reference to IMD 102, processors and memory devices are well known in the art, and the specific type and/or style of processor or memory device that can be used in external monitoring device 104 is not limited. Accordingly, processor 402 can be any suitable processing device currently known or hereinafter developed, and memory device 404 can be any suitable memory device currently known or hereinafter developed. In addition, communication circuitry 406 is circuitry that allows external monitoring device 104 to communicate with IMD 102 and other devices, such as external computing device 106, and/or sensor/therapy circuitry 112. Thus, if IMD 102 and the other devices are communicating via an RF connection, communication circuitry 406 comprises RF communication circuitry, as well. Similarly, if optical or acoustic communication connections are used, communication circuitry 406 is adapted to facilitate such connections. Further, in some embodiments, IMD 102 might be communicating with external monitor 104 via one type of communication connection, while other devices, such as external computing device 106 or sensor/therapy circuitry 112 might be communicating with external monitor 104 via other types of connections. Thus, communication circuitry 406 can be any circuitry adapted to facilitate the communications with IMD 102, external computing device 106, and sensor/therapy circuitry 112, and communication circuitry 406 can facilitate multiple types of communications at the same time. As one skilled in the art will appreciate, such circuitry is known in the art, and therefore, will not be discussed in detail herein.

In one embodiment, external monitoring device 104 also can include a patient interface 408 adapted to communicate information, such as therapy or diagnostic information, to the patient. In accordance with this embodiment, patient interface 408 may comprise a visually readable screen that allows the patient to read information, an audible or sound interface that can broadcast or transmit audible or sound information to the patient, or some other communication means.

Finally, referring again to FIG. 1, external computing device 106 can be any suitable computing device adapted to communicate with IMD 102, external monitoring device 104, and/or sensor/therapy circuitry 112, and process data from those devices. For example, in the case of a cardiac rhythm management ("CRM") IMD (e.g., pacemaker, ICD, etc.), external computing device 106 might be a programmer used by physicians, specialists, or other health care providers to extract data from the cardiac IMDs. Programmers are well known in the art. In addition, in other embodiments, external computing device 106 can be a repeater device associate with a patient. Examples of one or more repeater-type devices are disclosed in U.S. Pat. No. 6,607,485, issued on Aug. 9, 2003, and entitled "Computer Readable Storage Medium Containing Code for Automated Collection and Analysis of Patient Information Retrieved from an Implantable Medical Device for Remote Patient Care," the entirety of which is incorporated by reference herein for all purposes. In still other embodiments, external computing device 106 can be any other computing device for receiving, processing and/or storing medical data, including a workstation or appliance on a network, a server on a network, or a computer network as a whole. The present invention is not limited to any particular type of computing device.

Backend computing system 108 can be any type of computing system. In one embodiment, backend computing system is a networked system with a database operable to receive information regarding patients and their IMDs. The information then can be accessed by third parties, such as physicians, specialists, IMD manufacturers, insurance companies, pharmaceutical companies, or any other health care provider. As discussed in more detail below, backend computing system 108 can be configured to receive relative physiologic parameter values for patients and IMDs, other IMD information, and/or patient therapy information. In addition, backend computing system 108 can be configured to receive physiologic measurements and calculate relative measurements using ambient condition values. Further, backend computing system can determine patient therapy information based on data received from IMD 102, external monitor 104, and/or external computing device 106. Examples of embodiments of a one or more backend computing systems that can be used with the present invention are disclosed in U.S. Pat. No. 6,607,485 discussed above, and U.S. patent application Ser. No. 10/789,964, filed on Feb. 27, 2004, and entitled "Systems and Methods for Automatically Collecting, Formatting and Storing Medical Device Data in a Database," both of which are incorporated by reference herein for all purposes.

Figure 5:
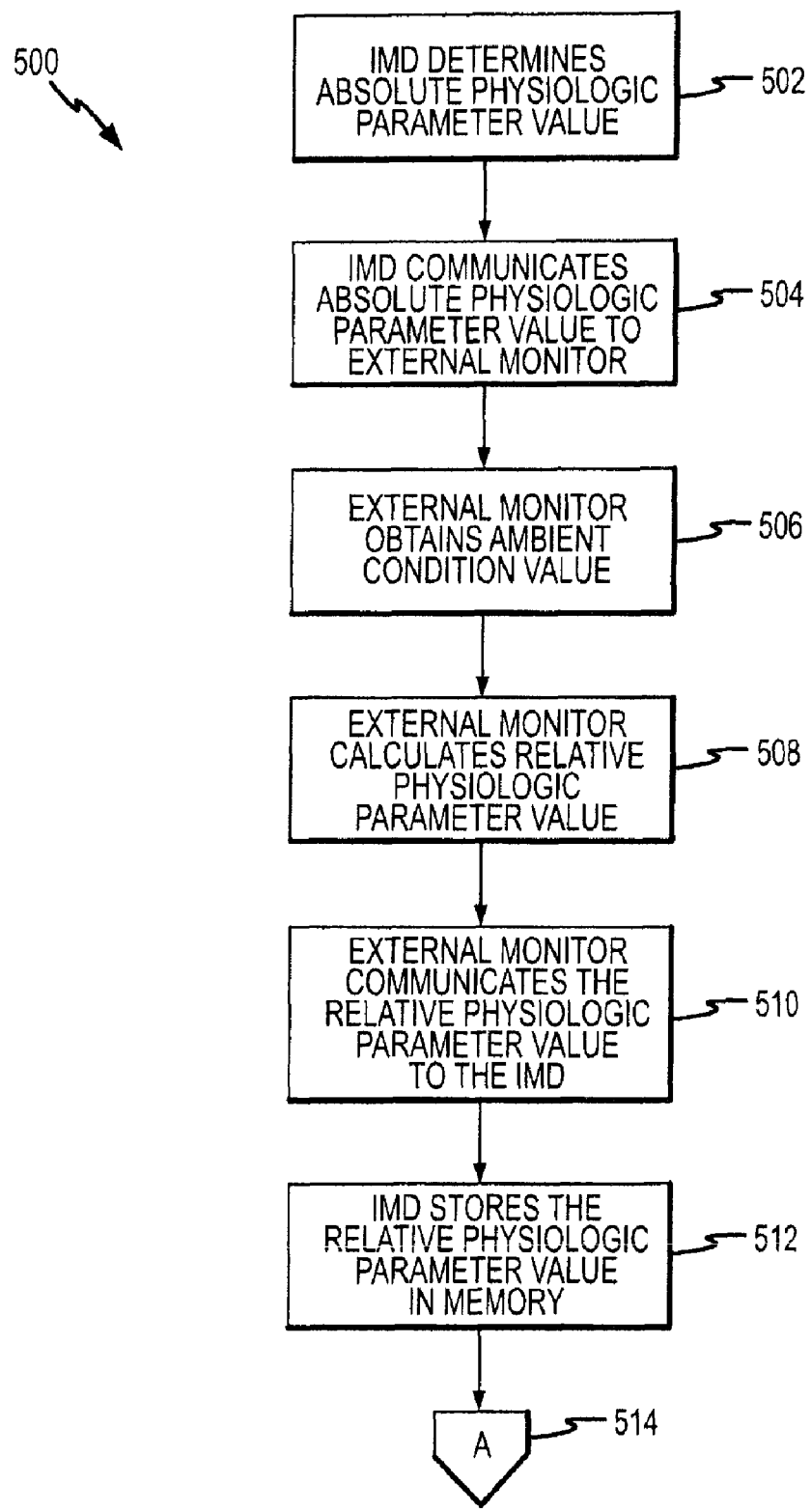

Referring now to FIG. 5, flow chart 500 illustrates a method for obtaining and using relative physiologic parameter values in accordance with one embodiment of the present invention. In accordance with the method illustrated in flow chart 500, an IMD (e.g., IMD 102 in FIG. 1) determines an absolute physiologic parameter value (block 502). As discussed above, the physiologic parameter values obtained can be any physiologic measurement, such as, blood pressure, temperature, blood or fluid flow, strain, electrical, chemical or magnetic properties within the body, or the like. In one particular embodiment, the physiologic parameter value obtained is blood pressure (e.g., intravascular or intracardiac blood pressure), and one or more pressure sensors are used to obtain the absolute blood pressure value. As one skilled in the art will appreciate, the absolute pressure measured by a pressure sensor typically is not a true absolute pressure. The measured pressure typically is adjusted for internal temperatures and/or a built-in backing pressure and/or temperature coefficients of the pressure sensor. Thus, an absolute blood pressure value can be calculated according to the following formula:

$$P_{ABP} = P_{MBP} - P_{Ref}(T_{Blood}) \text{ where:}$$

$P_{ABP}$ is the absolute blood pressure;
$P_{MBP}$ is the measured blood pressure; and
$P_{Ref}(T_{Blood})$ is the sensor reference/backing pressure, which is a function of blood temperature ($T_{Blood}$).

As one skilled in the art will appreciate, most pressure sensors are configured to perform these adjustments automatically, and thus, special processing within the IMD typically is not needed to obtain the absolute blood pressure value.

After the IMD obtains the absolute physiologic parameter (e.g., absolute blood pressure), the IMD communicates the absolute physiologic parameter value to an external monitor (e.g., external monitor 104 in FIG. 1) (block 504). In one embodiment, the IMD and the external monitor can implement a data transmission check (e.g., a cyclic redundancy code ("CRC") check) to ensure the data is transmitted properly.

The external monitor receives the absolute physiologic parameter value and obtains an ambient condition value (block 506). In some embodiments, the external monitor can obtain the ambient condition value either prior to or after receiving the absolute physiologic parameter value. In one embodiment, the external monitor includes a sensor for measuring the ambient condition value. Alternatively, in another embodiment, the external monitor could receive the ambient condition value from another source, such as another computing device in communication with the external monitor, the Internet, or some other source. The means by which the external monitor obtains the ambient condition value is not critical, and thus, the present invention is not limited to any particular method or system for obtaining the ambient condition value.

In some embodiments, the step of determining the absolute physiologic parameter value and the step of obtaining the ambient condition value may not occur at the same time or even close to the same time. For example, the external monitor may only measure or obtain the ambient condition value a few times a day, or there may be a delay between when the external monitor receives the ambient condition value and the absolute physiologic parameter value. As one skilled in the art will appreciate, ambient condition values can change relatively quickly, and thus, if an ambient condition value is not obtained at a time relatively close to when the absolute physiologic parameter value is obtained, the calculated relative value may be inaccurate. Therefore, the absolute physiologic parameter value and/or the ambient condition value can include a time stamp, so that values measured or obtained at about the same time can be used to calculate the relative physiologic parameter value. In some embodiments, if there is a gap between when ambient condition values are measured or obtained, averaged or pro rated ambient values can be used.

As discussed above, in one embodiment, the systems and methods of the present invention can be used to obtain blood pressure. In accordance with this embodiment, the ambient condition value is atmospheric or barometric pressure (and/or other parameters, such as temperature, humidity, altitude, etc. that can affect barometric pressure), which can be measured by one or more sensors in the external monitor, or which can be passed to the external monitor from an outside source. As with the pressure sensor associated with the IMD, a pressure sensor in the external monitor also typically is adjusted for temperature and a built-in backing pressure. Thus, in one embodiment, the atmospheric pressure obtained by the external monitor can be calculated according to the following formula:

$$P_{ATM} = P_{MATM} - P_{ATM\,Ref}(T_{ATM})\text{ where:}$$

$P_{ATM}$ is the adjusted atmospheric pressure;
$P_{MATM}$ is the measured atmospheric pressure; and
$P_{ATM\,Ref}(T_{ATM})$ is the sensor reference/backing pressure, which is a function of the temperature where the external monitor is placed ($T_{ATM}$).

As discussed above, most pressure sensors are configured to perform these adjustments automatically, and thus, special processing within the external monitor typically is not needed to obtain the adjusted atmospheric pressure.

After the external monitor obtains the ambient condition value and the absolute physiologic parameter value, the external monitor calculates a relative physiologic parameter value (block 508). For example, for intravascular blood pressure, a gauge blood pressure can be calculated by subtracting the atmospheric pressure from the absolute pressure value. When pressure sensor adjustments are taken into account, the following formula will apply:

$$P_{Gauge} = (P_{MBP} - P_{Ref}(T_{Blood})) - (P_{MATM} - P_{ATM\,Ref}(T_{ATM}))$$

In other embodiments, the relative physiologic parameter values can be calculated using other mathematical operations or models. For example, in one embodiment, some vascular abnormalities, which can be precursors to some cardiac problems, can be diagnosed by measuring physiologic parameters in two or more locations within the body, using two or more separate sensors. The data from the multiple sensors then might undergo mathematical manipulation, which then can be reconciled with the external ambient condition measurements. Thus, the present invention is not limited to a pure subtraction operation. Further, as one skilled in the art will appreciate, the calculations needed to obtain relative physiologic parameter values from other types of physiologic measurements (e.g., temperature, pH, etc.) may be different depending on the measurements being taken. Also, as discussed briefly above, if the physiologic parameter value and/or the ambient condition value include time stamps, the external monitor will use values that are similar in time (or averaged or pro rated values), so that the relative value is accurate.

In one embodiment, after the external monitor calculates the relative physiologic parameter value, it communicates the relative value to the IMD (block 510), which, in turn, stores the relative physiologic parameter value in a memory (block 512). Again, the IMD and the external monitor can implement a data transmission check, such as a CRC check, to ensure the data is transmitted properly. After the relative physiologic parameter value is stored in the IMD memory, the IMD and/or the external monitor can perform a number of different operations with the relative value. This is illustrated by continuation block 514 in FIG. 5.

Referring now to FIGS. 6*a*-6*d*, additional embodiments of the present invention will be described with reference to flow charts 600, 610, 620 and 630, respectively. In FIGS. 6*a*-6*d*, continuation blocks 602, 612, 622 and 632 are continuations from block 514 in FIG. 5. Thus, in accordance with the embodiment illustrated in FIG. 5*a*, after the IMD stores the relative physiologic parameter value in memory, the IMD can be configured to communicate the relative physiologic parameter value to an external computing device, such as external computing device 106 discussed above with reference to FIG. 1 (block 604). For example, in the case in which the IMD is a CRM device, such as a pacemaker or an ICD, the IMD can communicate the relative physiologic measurements to an external programmer or repeater device along with other IMD data, which is well known. A physician or other health care provider can analyze the relative physiologic measurements to determine trends and provide diagnosis and treatment based on those trends. In addition, the data can be uploaded to one or more backend systems (e.g., backend system 108) for later processing, access, and/or analysis by one or more health care providers, such as physicians, specialists, IMD manufacturers, insurance companies, pharmaceutical companies, or any other suitable health care provider (block 606).

Figure 6A:
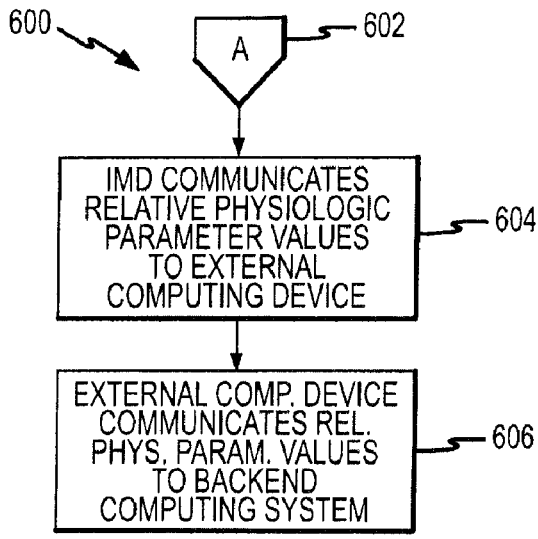
Figure 6B:
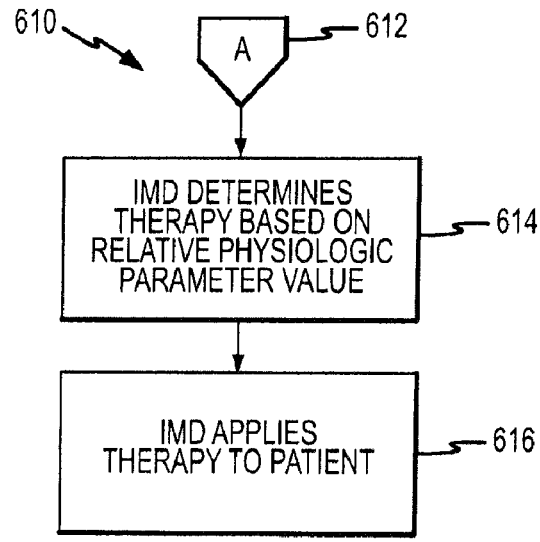

Referring now to FIG. 6*b*, in this particular embodiment, the IMD can be configured to calculate or determine a therapy based on the relative physiologic parameter value (block 614), and then administer the therapy to the patient (block 616). For example, if the IMD is a cardiac pacemaker, the pacemaker may be configured to change pacing modes or parameters based on the obtained relative physiologic value. Similarly, if the IMD is a drug delivery device, the device might deliver a drug dosage when certain relative physiologic parameter values are measured. As one skilled in the art will appreciate, the type of therapy administered to the patient will be dependent upon the type of IMD used and the physiologic measurements taken. Thus, as discussed above, the present invention is not limited to any particular IMD or therapy system.

Figure 6C:
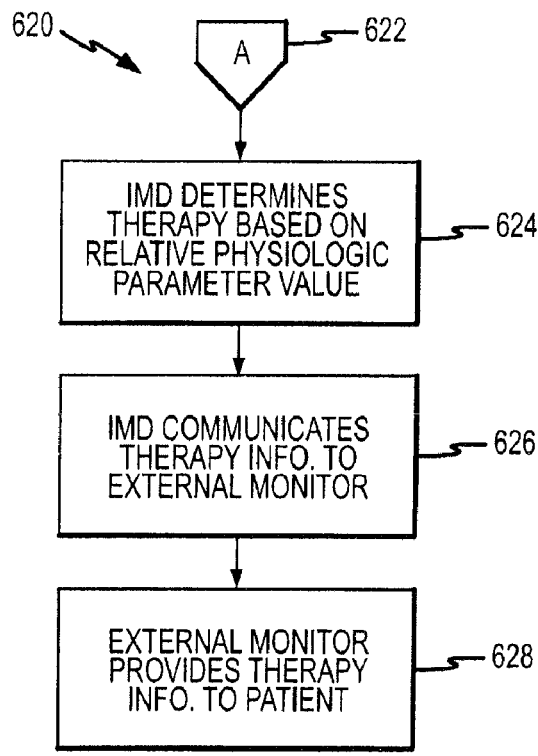

Referring now to FIG. 6*c*, in this particular embodiment, the IMD can be configured to calculate or determine a therapy or therapy information based on the relative physiologic parameter value (block 624). The IMD then is configured to communicate the therapy information to the external monitor (e.g., external monitor 104) (block 626), which in turn can be configured to provide or communicate the therapy information to the patient (block 628). For example, in the case of a CRM IMD, which is configured to detect blood pressure, when the IMD detects a consistent rise in blood pressure for a congestive heart failure patient, the IMD can be configure to communicate information to the patient on how to deal with the situation. For example, the IMD might communicate a message to the external monitor, instructing the patient to change a medication dosage, or perhaps take a medication. As discussed above, the external monitor can include a communication interface, such as a visual screen or audible interface, to communicate the information to the patient.

Figure 6D:
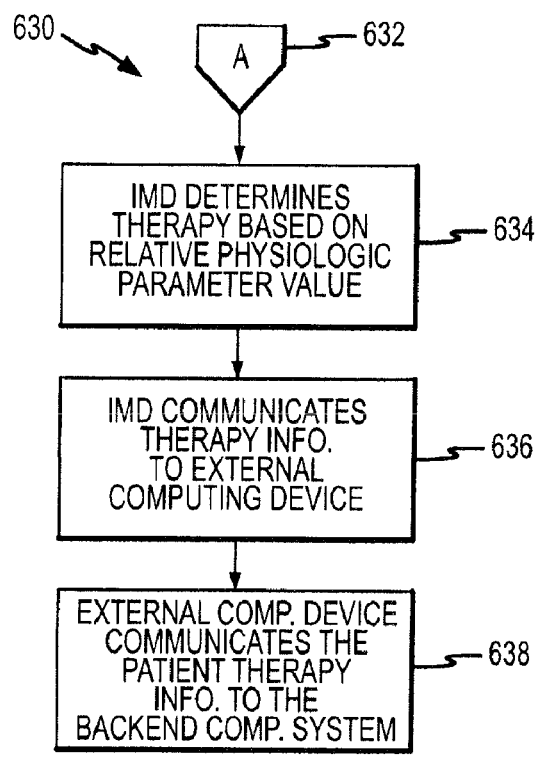

Referring now to FIG. 6d, in this particular embodiment, the IMD again can be configured to calculate or determine a therapy or therapy information based on the relative physiologic parameter value (block 634). Then, in stead of, or in addition to administering the therapy to the patient, the IMD is configured to communicate the therapy information to an external computing device, such as computing device 106 (block 636). A physician or other health care provider then can analyze the therapy information and provide it to the patient if the physician determines that it is appropriate, or the physician can provide different or additional therapy to the patient if the physician determines that an alternative therapy would be better. In addition, the therapy information can be uploaded to a backend computing system (e.g., backend computing system 108) for later processing, access and/or analysis.

In an alternative embodiment, instead of the external monitor communicating the relative physiologic parameter value to the IMD, it can be configured to communicate the relative physiologic parameter value to the external computing device without first communicating it to the IMD. The external computing device then can communicate it to a backend computing system, or it can display it to the patient or another health care provider. In addition, instead of the IMD determining the therapy information, the external monitor or the external computing device can be configured to determine the therapy information based on, in part, the calculated relative physiologic parameter value. In this embodiment, the processor within the external monitor or the external computing device will include the therapy logic, not the processor within the IMD. In addition, as one skilled in the art will appreciate, the therapy and/or diagnosis information that the IMD, the external monitor, and/or the external computing device provide to the patient will depend upon the type of IMD and the type of physiologic parameters being measured. As discussed above, the present invention is not limited to any particular IMD or physiologic parameter value measurement.

Figure 7:
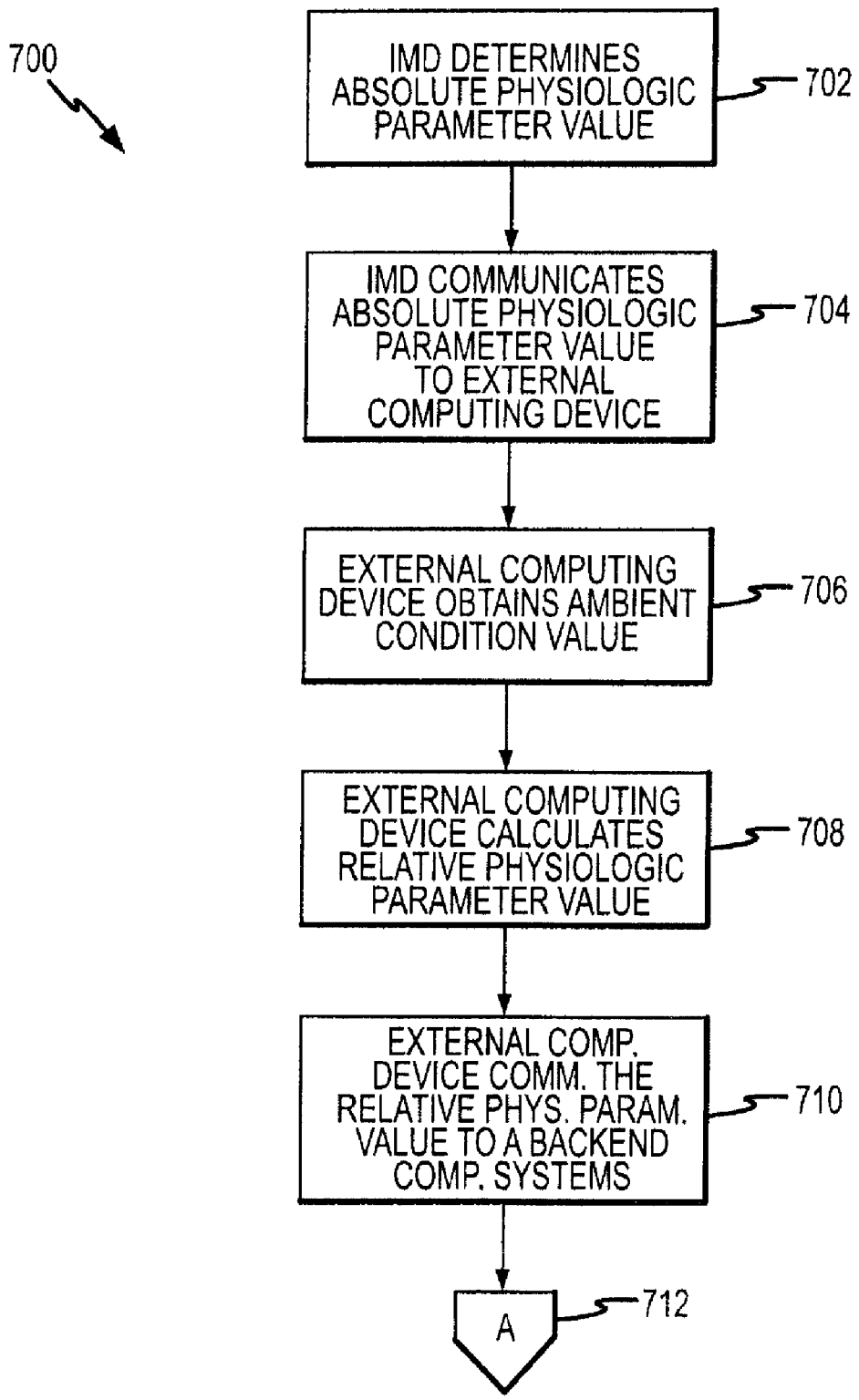

Referring now to FIG. 7, an alternative embodiment of a method of deriving and using relative physiologic parameter values is shown. In accordance with the method illustrated in flow chart 700, an IMD (e.g., IMD 102 in FIG. 1) determines an absolute physiologic parameter value (block 702). As discussed above, the physiologic parameter values obtained can be any physiologic measurement, such as, blood pressure, temperature, blood or fluid flow, strain, electrical, chemical or magnetic properties within the body, or the like. In one particular embodiment, the physiologic parameter value obtained is blood pressure (e.g., intravascular or intracardiac blood pressure), and one or more pressure sensors are used to obtain the absolute blood pressure value. As discussed above, the absolute pressure measured by a pressure sensor can be adjusted for internal temperatures and/or a built-in backing pressure and/or temperature coefficients of the pressure sensor.

After the IMD obtains the absolute physiologic parameter (e.g., absolute blood pressure), the IMD communicates the absolute physiologic parameter value to an external computing device (e.g., external computing device 106 in FIG. 1) (block 704). In one embodiment, the IMD and the external computing device can implement a data transmission check (e.g., a cyclic redundancy code ("CRC") check) to ensure the data is transmitted properly.

The external computing device receives the absolute physiologic parameter value and obtains an ambient condition value (block 706). In one embodiment, the external computing device includes one or more sensors for measuring the ambient condition value. Alternatively, in another embodiment, the external computing device can receive the ambient condition value from another source, such as another computing device in communication with the external computing device, the Internet, or some other source. For example, as discussed above, an external monitor (e.g., external monitor 104 in FIG. 1) can include a sensor for measuring the ambient condition value, and the external monitor can pass the ambient condition value to the external computing device via a wired or wireless communication connection. The means by which the external computing device obtains the ambient condition value is not critical, and thus, the present invention is not limited to any particular method or system for obtaining the ambient condition value.

In one embodiment, the systems and methods of the present invention can be used to obtain blood pressure. In accordance with this embodiment, the ambient condition value is atmospheric or barometric pressure, which can be measured by one or more sensors in the external computing device, or which can be passed to the external computing device from an outside source (e.g., from an external monitor). As with the pressure sensor associated with the IMD, a pressure sensor in the external computing device or the external monitor also typically is adjusted for temperature and a built-in backing pressure. As mentioned above, most pressure sensors are configured to perform these adjustments automatically, and thus, special processing within the external computing device or the external monitor typically is not needed to obtain the adjusted atmospheric pressure.

After the external computing device obtains the ambient condition value, the external computing device calculates a relative physiologic parameter value (block 708). In one embodiment, for blood pressure, a gauge blood pressure can be calculated by subtracting the atmospheric pressure from the absolute pressure value, or as discussed above, other mathematical calculations can be used. In addition, the calculations needed to obtain relative physiologic parameter values from other types of physiologic measurements (e.g., temperature, pH, etc.) may be different depending on the measurements being taken. Further, as discussed above, the physiologic parameter value and/or the ambient condition value can include time stamps, so that the relative physiologic parameter value is calculated using values that are similar in time.

In one embodiment, after the external computing device calculates the relative physiologic parameter value, it communicates the relative value to a backend computing system (e.g., backend computing system 108 in FIG. 1) (block 710). Further, the external computing device can display or provide the relative physiologic measurement values to a health care provider or other entity for review. For example, in the case in which the IMD is a CRM device, such as a pacemaker or an ICD, the external computing device might be an external programmer with print-out or display capabilities. Thus, a physician or other health care provider can view and analyze the relative physiologic measurements to determine trends and provide diagnosis and treatment based on those trends.

After the relative physiologic parameter value is communicated to the backend computing system, additional processing can occur in a number of different devices in the system. This is illustrated by continuation block 712 in FIG. 7.

Referring now to FIGS. 8a-8d, additional embodiments of the present invention will be described with reference to flow charts 800, 810, 820 and 830, respectively. In FIGS. 8a-8b, continuation blocks 802 and 812 are continuations from block 712 in FIG. 7. Thus, in accordance with the embodiment illustrated in FIG. 8a, after the external computing device communicates the relative physiologic parameter value to the backend computing system, the backend computing system stores the relative physiologic parameter values, for example, in a database (block 804). The data then can be made available for later processing, access, and/or analysis by one or more health care providers, such as physicians, specialists, IMD manufacturers, insurance companies, pharmaceutical companies, or any other suitable health care provider (block 806).

As illustrated by flow chart 810 in FIG. 8b, the external computing device also can communicate the relative physiologic parameter value to the IMD (block 814), which then stores the relative physiologic parameter value in memory (block 816). When the IMD receives the relative physiologic parameter value, the IMD then can use the value for additional processing, as illustrated by continuation block 818. Continuation blocks 822 and 832 in FIGS. 8c and 8d, respectively, continue from block 818. Also, even though the drawings illustrate that the relative physiologic parameter value is communicated to the backend computing system and then to the IMD, the present invention is not limited to this embodiment. In some embodiments, the external computing device can display the relative physiologic parameter value to a physician or other user, or it can determine therapy information using the relative physiologic parameter value without first communicating the relative value to the backend computing system. Further, the external computing device can communicate the relative physiologic parameter value to the IMD without first communicating it to the backend computing system. Thus, as one skilled in the art will appreciate, the present invention is not limited to the illustrated embodiments.

Referring now to FIG. 8c, in this particular embodiment, the IMD can be configured to calculate or determine a therapy based on the relative physiologic parameter value (block 824). In one embodiment, the IMD can be configured to administer the therapy to the patient (block 826), as discussed above.

Referring now to FIG. 8d, in this particular embodiment, the IMD again can be configured to calculate or determine a therapy or therapy information based on the relative physiologic parameter value (block 834). Then, in stead of, or in addition to administering the therapy to the patient, the IMD is configured to communicate the therapy information to the external computing device (e.g., external computing device 106), or alternatively, the external monitor (e.g., external monitor 104) (block 836). In one embodiment, the external computing device (and/or external monitor) can be configured to provide or communicate the therapy information to the patient via a user or patient interface, as discussed above (block 838).

In an alternative embodiment, after the external computing device (or external monitor) receives the therapy information from the IMD, a physician or other health care provider then can analyze the therapy information and provide it to the patient if the physician determines that it is appropriate, or the physician could provide different or additional therapy to the patient if the physician determines that an alternative therapy would be better. In addition, the therapy information can be uploaded to a backend computing system (e.g., backend computing system 108) (block 840) for later processing, access and/or analysis. Also, instead of the IMD determining the therapy information, the external computing device, the external monitor, and/or the backend computing system can be configured to determine the therapy information based on the relative physiologic parameter value. The present invention is not limited to the IMD determining the therapy.

Figure 9:
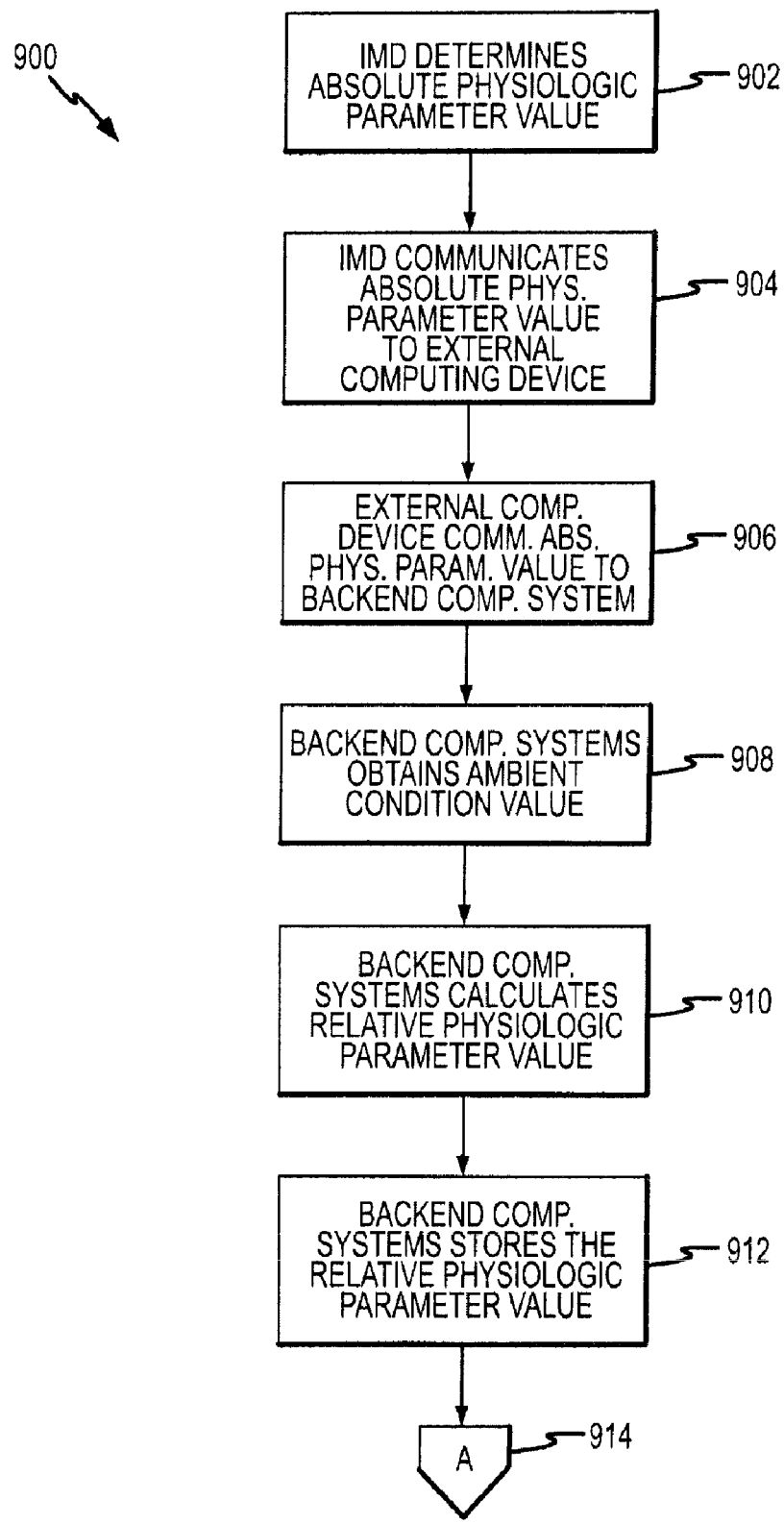

Referring now to FIG. 9, yet another embodiment of a method of deriving and using relative physiologic parameter values is shown. In accordance with the method illustrated in flow chart 900, an IMD (e.g., IMD 102 in FIG. 1) determines an absolute physiologic parameter value (block 902). As discussed above, the physiologic parameter values obtained can be any physiologic measurement, such as, blood pressure, temperature, blood or fluid flow, strain, electrical, chemical or magnetic properties within the body, or the like.

After the IMD obtains the absolute physiologic parameter (e.g., absolute blood pressure), the IMD communicates the absolute physiologic parameter value to an external computing device (e.g., external computing device 106 in FIG. 1) (block 904). Again, the IMD and the external computing device can implement a data transmission check (e.g., a cyclic redundancy code ("CRC") check) to ensure the data is transmitted properly.

The external computing device receives the absolute physiologic parameter value and communicates it to a backend computing system (e.g., backend computing system 108 in FIG. 1) (block 906). The backend computing then obtains an ambient condition value (block 908), for example, from the external computing device or from an external monitor, as discussed above. Alternatively, the backend computing system can receive the ambient condition value from another source, such as another computing device in communication with the backend computing system, the Internet, or some other source. The means by which the backend computing system obtains the ambient condition value is not critical, and thus, the present invention is not limited to any particular method or system for obtaining the ambient condition value. Also, as one skilled in the art will appreciate, backend computing system can obtain the ambient condition value prior to receiving the absolute physiologic parameter value. In addition, as discussed above, the physiologic parameter value and/or the ambient condition value can include time stamps, so that the relative physiologic parameter value is calculated using values that are similar in time.

After the backend computing system obtains the ambient condition value and the absolute physiologic parameter value, the backend computing system calculates a relative physiologic parameter value (block 910), and then the backend computing system stores the relative physiologic parameter value, for example, in a database or other similar storage area (block 912). The data then can be made available for later processing, access, and/or analysis by one or more health care providers, such as physicians, specialists, IMD manufacturers, insurance companies, pharmaceutical companies, or any other suitable health care provider.

After the relative physiologic parameter value is calculated at the backend computing system, additional processing can occur in a number of different devices in the system. This is illustrated by continuation block 914 in FIG. 9.

Figure 10A:
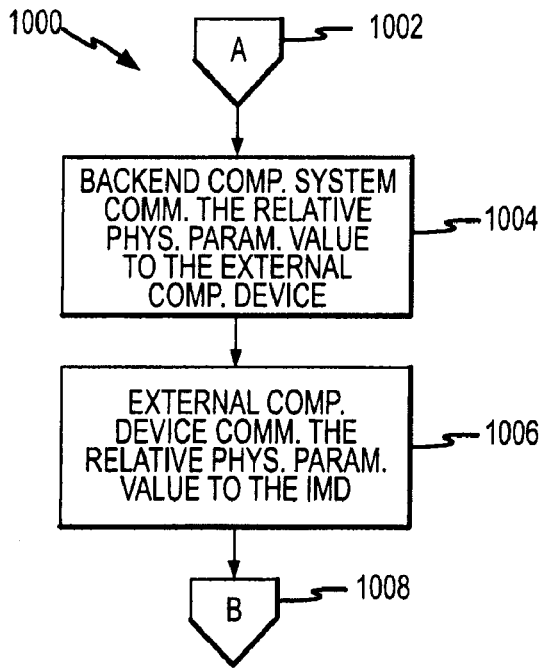
Figure 10B:
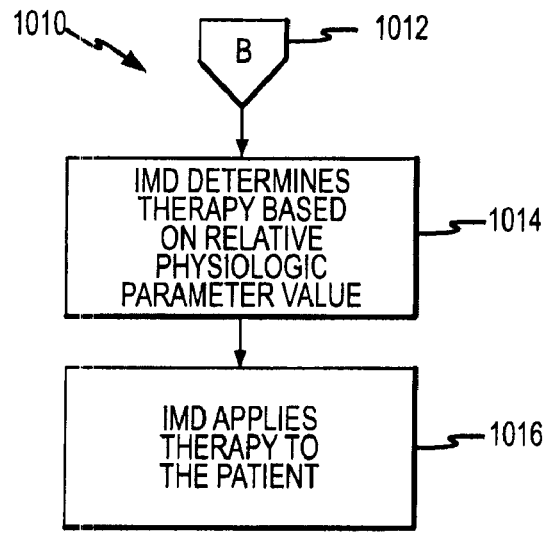

Referring now to FIGS. 10a-10d, additional embodiments of the present invention will be described with reference to flow charts 1000, 1010, 1020 and 1030, respectively. In FIGS. 10a-10b, continuation blocks 1002 and 1032 are continuations from block 914 in FIG. 9. Thus, in accordance with the embodiment illustrated in FIG. 10a, after the backend computing system calculates the relative physiologic parameter value, it communicates the relative physiologic parameter value to the external computing device. As discussed above, the external computing device then can display or provide the relative physiologic measurement values to a health care provider or other entity for review.

In addition, as illustrated by flow chart 1000 in FIG. 10*a*, the external computing device also can communicate the relative physiologic parameter value to the IMD (block 1006), which then can store the relative physiologic parameter value, for example, in a memory. When the IMD receives the relative physiologic parameter value, the IMD then can use the value for additional processing, as illustrated by continuation block 1008. Continuation blocks 1012 and 1022 in FIGS. 10*b* and 10*c*, respectively, continue from block 1008.

Referring now to FIG. 10*b*, in this particular embodiment, the IMD can be configured to calculate or determine a therapy based on the relative physiologic parameter value (block 1014). As discussed above, the IMD can be configured to administer the therapy to the patient (block 1016).

Figure 10C:
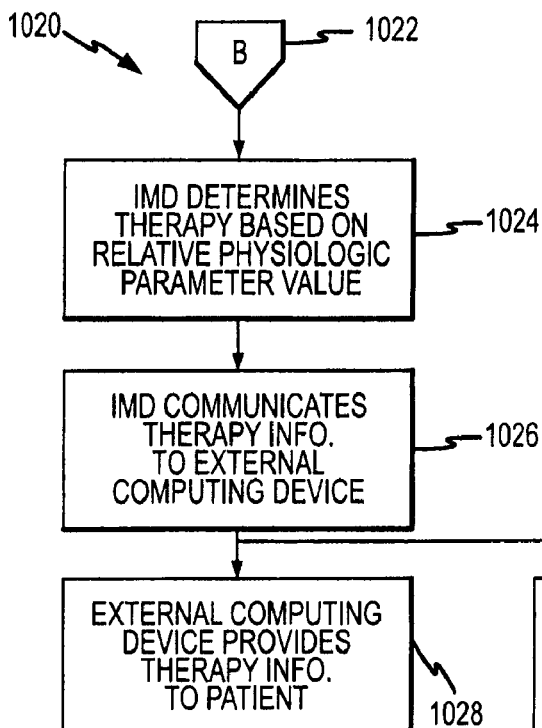

In an alternative embodiment illustrated in FIG. 10*c*, the IMD again can be configured to calculate or determine a therapy or therapy information based on the relative physiologic parameter value (block 1024), but in stead of, or in addition to administering the therapy to the patient, the IMD is configured to communicate the therapy information to the external computing device or external monitor (block 1026), which can be configured to provide or communicate the therapy information to the patient (block 1028).

Further, as discussed above, after the external computing device (and/or the external monitor) receives the therapy information from the IMD, a physician or other health care provider then can analyze the therapy information and provide it to the patient if the physician determines that it is appropriate, or the physician could provide different or additional therapy to the patient if the physician determines that an alternative therapy would be better. The therapy information also can be uploaded to a backend computing system (e.g., backend computing system 108) (block 1029) for later processing, access and/or analysis. In addition, in an alternative embodiment, instead of the IMD determining the therapy information, the external computing device and/or the external monitor can be configured to calculate or determine the therapy information.

Figure 10D:
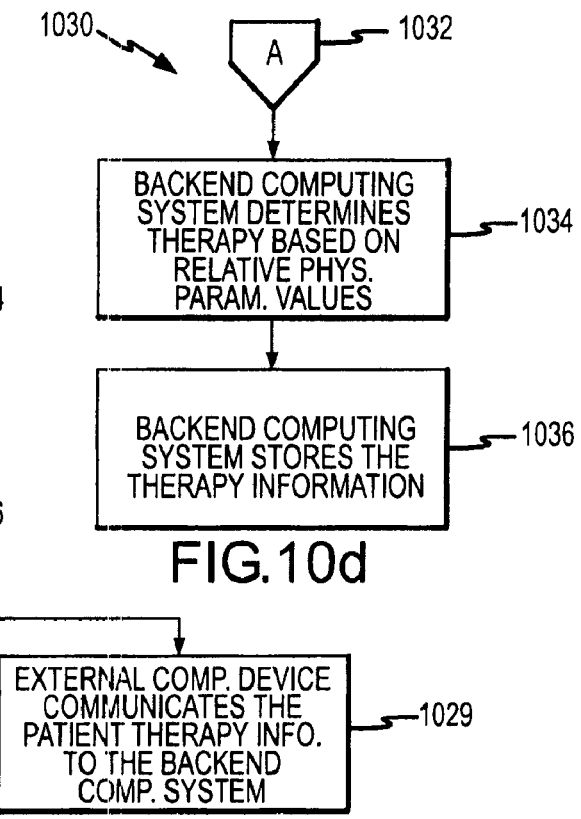

Referring now to FIG. 10*d*, flowchart 1030 illustrates another embodiment of the present invention. In accordance with this particular embodiment, after the backend computing system calculates the relative physiologic parameter value, the backend computing system then can use that value to determine a therapy or therapy information for the patient (block 1034). The backend system then can store the therapy information in the database for later access by a health care provider (block 1036). In addition, the backend system can communicate the therapy information to the external computing device and/or the external monitor, which can display or provide the therapy information to a health care provider, as discussed above.

Figure 11:
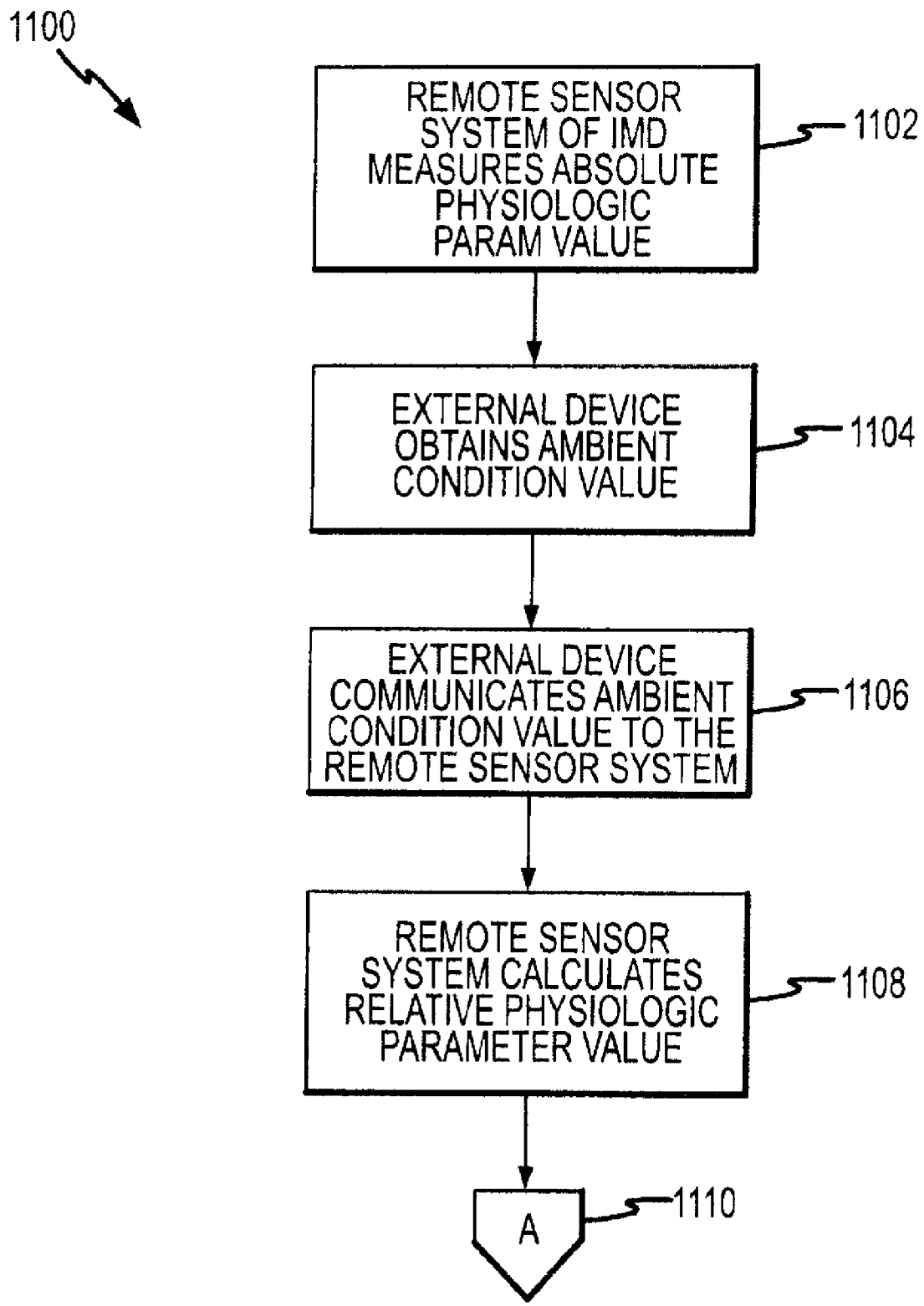

Referring now to FIG. 11, still another embodiment of a method of deriving and using relative physiologic parameter values is shown. In accordance with the method illustrated in flow chart 1100, a remote sensor system of an IMD (e.g., remote sensor system 112 in FIG. 1) measures an absolute physiologic parameter value (block 1102). As discussed above, the remote sensor system can comprises satellite sensors, which can measure any physiologic measurement, such as, blood pressure, temperature, blood or fluid flow, strain, electrical, chemical or magnetic properties within the body, or the like. In one particular embodiment, the physiologic parameter value obtained is blood pressure (e.g., intravascular or intracardiac blood pressure), and one or more pressure sensors associated with the remoter sensor system are used to obtain the absolute blood pressure value. Again, the absolute pressure measured by a pressure sensor can be adjusted for internal temperatures and/or a built-in backing pressure and/or temperature coefficients of the pressure sensor.

After the remote sensor system of the IMD obtains the absolute physiologic parameter (e.g., absolute blood pressure), an external device obtains an ambient condition value (block 1104). In one embodiment, the external device is an external monitor (e.g., external monitor 104 in FIG. 1), which includes one or more sensors for measuring the ambient condition value. In another embodiment, the external device is an external computing device (e.g., external computing device 106 in FIG. 1), which can either measure the ambient condition value, or obtain the ambient condition value from another source, such as a backend computing system, other sensors in communication with the external computing device, or the Internet.

After the external device obtains the ambient condition value, it communicates the ambient condition value to the remote sensor system (block 1106), which then calculates a relative physiologic parameter value from the absolute physiologic parameter value and the ambient condition value (block 1108). As with other communication connections, the external device and the remote sensor system can implement a data transmission check (e.g., a cyclic redundancy code ("CRC") check) to ensure the data is transmitted properly. Further, as discussed above, the physiologic parameter value and/or the ambient condition value can include time stamps, so that the relative physiologic parameter value is calculated using values that are similar in time. After the remote sensor system calculates the relative physiologic parameter value, additional processing can occur in a number of different devices in the system. This is illustrated by continuation block 1110 in FIG. 11.

Referring now to FIGS. 12*a*-12*f*, additional embodiments of the present invention will be described with reference to flow charts 1200-1250. In accordance with the embodiment illustrated in FIG. 12*a*, after the remote sensor system calculates the relative physiologic parameter value, it communicates the relative physiologic parameter value to the main body of the IMD (e.g., IMD 102) (block 1204), which then can store the relative physiologic parameter value, for example, in a memory (block 1206).

Figure 12A:
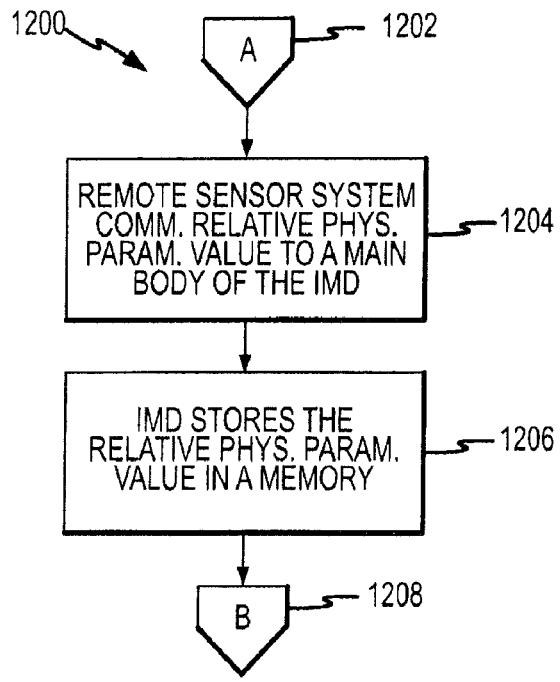
Figure 12B:
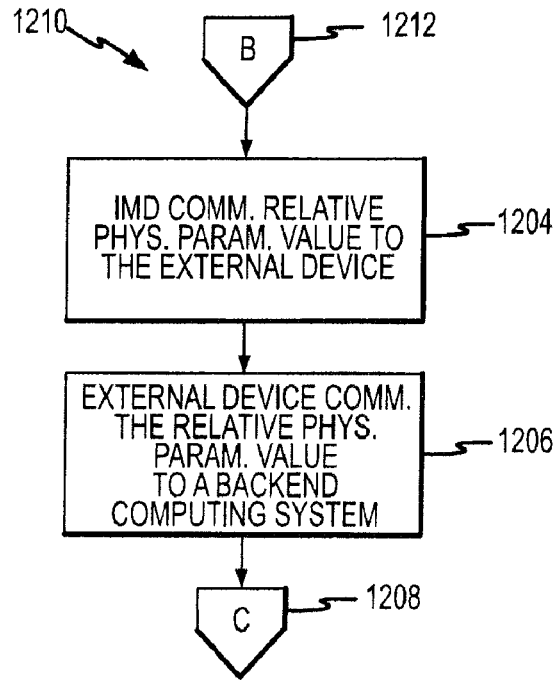

In addition, after the IMD receives the relative physiologic parameter value, it can communicate it to the external device (block 1214 in FIG. 12*b*). As discussed in previous embodiments, the external device can provide the relative physiologic parameter value to the patient or a health care provider, or it can communicate the relative physiologic parameter value to a backend computing system (block 1216).

Figure 12C:
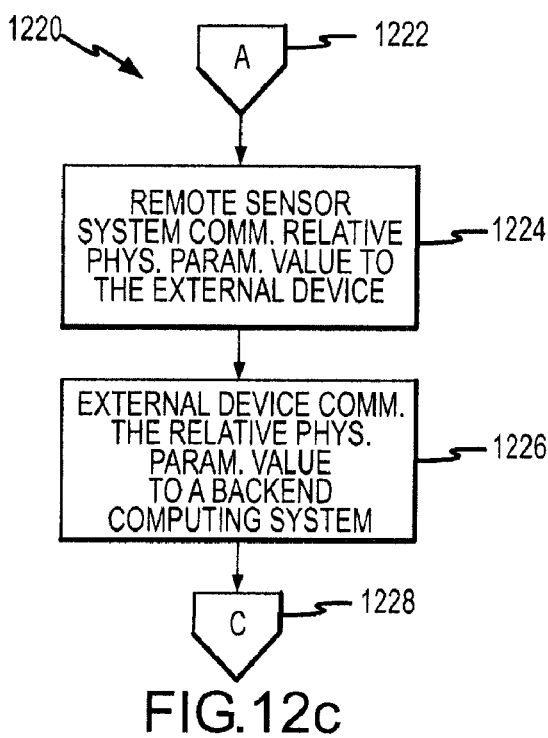

In another embodiment, instead of the main body of the IMD communicating the relative physiologic parameter value to the external device, the remote sensor system can be configured to communicate the relative physiologic parameter value to the external device directly (block 1224 in FIG. 12*c*). Then, as with the embodiment of FIG. 12*b*, the external device can display the relative physiologic parameter value, and/or it can communicate the value to a backend computing system (block 1226).

Upon receiving the relative physiologic parameter value, the backend computing system then can store the value in a database for access by health care providers. In addition, as discussed above, the backend computing system can use the relative physiologic parameter value to determine a therapy for the patient (block 1254 in FIG. 12f). The backend computing system then can store the therapy information in a database (block 1256), and/or the backend system can communicate the therapy information to the external device, which can display or provide the therapy information to relevant parties.

Referring now to FIGS. 12d and 12e, in accordance with other embodiments of the invention, after the IMD stores the relative physiologic parameter value (block 1206 in FIG. 12a), the IMD can be configured to calculate or determine a therapy based on the relative physiologic parameter value (blocks 1234 and 1244 in FIGS. 12d and 12e, respectively). As discussed above, the IMD can be configured to administer the therapy to the patient (block 1236), and/or the IMD can communicate the therapy information to the external device (block 1246). The external device then can provide or communicate the therapy information to the patient, a physician or other health care provider (block 1248). In addition, the therapy information can be uploaded to a backend computing system (block 1249) for later processing, access and/or analysis. In still other embodiments, instead of the backend computing system or the IMD determining the therapy information, the external device can be configured to calculate or determine the therapy.

In conclusion, the present invention provides novel systems, methods and arrangements for deriving relative physiologic parameter values from measured physiologic parameters and from ambient condition values. While detailed descriptions of one or more embodiments of the invention have been given above, various alternatives, modifications, and equivalents will be apparent to those skilled in the art without varying from the spirit of the invention. Therefore, the above description should not be taken as limiting the scope of the invention, which is defined by the appended claims.

What is claimed is:

1. A system for deriving relative physiologic measurement values, comprising:
an implantable medical device ("IMD") operable to determine an absolute physiologic parameter value within a patient's body and communicate the absolute physiologic parameter value outside the patient's body, the IMD including a main body and a remote sensor system adapted to be implanted in the patient's body, the main body including a receiver in acoustic communication with the remote sensor system, the remote sensor system operable to measure an absolute physiologic parameter value within the patient's body and including a transmitter adapted to acoustically communicate the absolute physiologic parameter value to the receiver;
an external computing device including communication circuitry configured to wirelessly receive the absolute physiologic parameter value and an integral sensor configured to sense an ambient condition value outside the patient's body, the external computing device comprising a single device operable to both:
wirelessly receive the absolute physiologic parameter value from the IMD; and
sense an ambient condition value outside the patient's body related to the absolute physiologic parameter value;
the external computing device or a backend computing system operable to:
calculate a relative physiologic parameter value from the ambient condition value and the absolute physiologic parameter value; and
store the calculated relative physiologic parameter value.

2. The system as recited in claim 1, wherein the external computing device is operable to communicate the relative physiologic parameter value to the IMD, and wherein the IMD is further operable to receive the relative physiologic parameter value and store it in a memory.

3. The system as recited in claim 2, wherein the IMD is operable to provide therapy to a patient, and wherein the IMD uses the relative physiologic parameter value to determine the proper therapy to provide to the patient.

4. The system as recited in claim 3, wherein the therapy is selected from the group consisting of cardiac pacing therapy, anti-tachycardia therapy, drug delivery therapy, neurostimulation therapy, and blood pump therapy.

5. The system as recited in claim 2, wherein:
the IMD comprises a processor operable to generate patient therapy information based at least in part on the relative physiologic parameter value;
the IMD is further operable to communicate the patient therapy information to the external computing device; and
the external computing device comprises a patient communication interface operable to provide the patient therapy information to the patient.

6. The system as recited in claim 2, wherein:
the IMD comprises a processor operable to generate patient therapy information based at least in part on the relative physiologic parameter value;
the IMD is further operable to communicate the patient therapy information to the external computing device; and
the external computing device is operable to communicate the patient therapy information to the backend computing system for access by one or more health care providers.

7. The system as recited in claim 1, wherein the backend computing system comprises a database accessible by one or more health care providers, and wherein the one or more health care providers can obtain the relative physiologic parameter value from the database and use the relative physiologic parameter value to provide a service to the patient selected from the group consisting of diagnosing the patient, prescribing medication to the patient, providing a therapy to the patient, or modifying one or more settings of the IMD.

8. The system as recited in claim 1, wherein the absolute physiologic parameter value comprises blood pressure, wherein the ambient condition value comprises an ambient pressure value, and wherein the relative physiologic parameter value comprises the blood pressure value relative to the ambient pressure value.

9. The system as recited in claim 8, wherein the blood pressure is intravascular or intracardiac blood pressure.

10. The system as recited in claim 1, wherein the external computing device comprises an IMD programmer.

11. The system as recited in claim 1, wherein the external computing device comprises a repeater device in communication with the backend computing system.

12. The system as recited in claim 1, wherein the IMD and the external computing device are operable to communicate via a wireless communication connection selected from the group consisting of: a radio frequency communication connection; an acoustic communication connection; an electrical field communication connection; and an optical communication connection.

13. The system as recited in claim 1, wherein the IMD is selected from the group consisting of a physiologic parameter sensor, a pacemaker, a defibrillator, a bi-ventricular pacer, a ventricular assist blood pump, a drug delivery pump, a drug infusion device, a neurostimulating device, an intra-ocular shunt, and an intra-cranial shunt.

14. The system as recited in claim 1, wherein the backend computing system is operable to determine a therapy to provide to a patient, and wherein the backend computing system uses the relative physiologic parameter value to determine the therapy, the backend computing system further being operable to store the therapy information for access by one or more health care providers.

15. A method for deriving relative physiologic measurement values, comprising:
    determining an absolute physiologic parameter value within a patient's body with an implantable medical device ("IMD"), the IMD including a main body with a receiver in acoustic communication with a remote sensor system, the remote sensor system including a transmitter adapted to acoustically communicate the absolute physiologic parameter value to the receiver;
    measuring the absolute physiologic parameter value with the remote sensor system and acoustically communicating the absolute physiologic parameter value to the receiver of the IMD;
    communicating the absolute physiologic parameter value to an external computing device outside the patient's body, the external computing device comprising a single device including communication circuitry configured to wirelessly receive the absolute physiologic parameter value and an integral sensor configured to sense an ambient condition value outside of the patient's body;
    sensing, via the sensor, an ambient condition value outside of the patient's body related to the absolute physiologic parameter value;
    communicating the absolute physiologic parameter value and the ambient condition value from the external computing device to a backend computing system;
    calculating a relative physiologic parameter value from the ambient condition value and the absolute physiologic parameter value; and
    storing the relative physiologic parameter value in a memory.

16. The method as recited in claim 15, further comprising the steps of:
    communicating the relative physiologic parameter value to the external computing device with the backend computing system; and
    storing the relative physiologic parameter value with the external computing device.

17. The method as recited in claim 16, further comprising the steps of:
    communicating the relative physiologic parameter value to the IMD; and
    storing the relative physiologic parameter value in a memory.

18. The method as recited in claim 17, wherein the steps of communicating the measured absolute physiologic parameter value to the external computing device and communicating the relative physiologic parameter value from the external computing device to the IMD comprise communicating via a wireless communication connection selected from the group consisting of: a radio frequency communication connection; an acoustic communication connection; an electric field communication connection; and an optical communication connection.

19. The method as recited in claim 17, further comprising:
    determining a therapy to provide to the patient using the relative physiologic parameter value; and
    providing the therapy to the patient with the IMD.

20. The method as recited in claim 19, wherein the therapy is selected from the group consisting of cardiac pacing therapy, anti-tachycardia therapy, drug delivery therapy, neurostimulation therapy, and blood pump therapy.

21. The method as recited in claim 17, further comprising:
    generating patient therapy information with the IMD based at least in part on the relative physiologic parameter value;
    communicating the patient therapy information from the IMD to the external computing device; and
    providing the patient therapy information to the patient with the external computing device via a communication interface.

22. The method as recited in claim 17, further comprising:
    generating patient therapy information with the IMD based at least in part on the relative physiologic parameter value;
    communicating the patient therapy information from the IMD to the external computing device; and
    communicating the patient therapy information to the backend computing system for access by one or more health care providers.

23. The method as recited in claim 15, further comprising the steps of:
    storing the relative physiologic parameter value in a database of the backend computing system accessible by one or more health care providers obtaining the relative physiologic parameter value from the database; and
    using the relative physiologic parameter value to provide a service to the patient selected from the group consisting of diagnosing the patient, prescribing medication to the patient, providing a therapy to the patient, or modifying one or more settings of the IMD.

24. The method as recited in claim 15, wherein the absolute physiologic parameter value comprises blood pressure, wherein the ambient condition value comprises an ambient pressure value, and wherein the relative physiologic parameter value comprises the blood pressure value relative to the ambient pressure value.

25. The method as recited in claim 24, wherein the blood pressure is intravascular or intracardiac blood pressure.

26. The method as recited in claim 15, wherein the step of obtaining an ambient condition value comprises the external computing device measuring the ambient condition value and communicating the ambient condition value to the backend computing system.

27. The method as recited in claim 15, wherein the external computing device comprises an IMD programmer.

28. The method as recited in claim 15, wherein the external computing device comprises a repeater device in communication with the backend computing system.

29. The method as recited in claim 15, wherein the IMD is selected from the group consisting of a physiologic parameter sensor, a pacemaker, a defibrillator, a bi-ventricular pacer, a ventricular assist blood pump, a drug delivery pump, a drug infusion device, a neurostimulating device, an intra-ocular shunt, and an intra-cranial shunt.

30. The method as recited in claim 15, further comprising:
    determining a therapy to provide to a patient using the relative physiologic parameter value; and
    storing the therapy information for access by one or more health care providers using the backend computing system.

31. A system for deriving relative blood pressure values, comprising:
an implantable medical device ("IMD") including:
a remote sensor system adapted to be implanted in a patient's body and operable to measure an internal blood pressure value, the remote sensor system including an acoustic transmitter;
a main body adapted to be implanted in the patient's body, the main body including a receiver in acoustic communication with the transmitter of the remote sensor system and operable to acoustically receive the internal blood pressure value from the remote sensor system, the main body operable to communicate the internal blood pressure value outside the patient's body;
an external computing device operable to:
wirelessly receive the internal blood pressure value from the IMD; and
communicate the internal blood pressure value to a backend computing system; and
the backend computing system operable to:
receive the internal blood pressure value from the external computing device;
obtain an ambient pressure value from an external monitor located outside the patient's body;
calculate a relative blood pressure value from the ambient pressure value and the internal blood pressure value; and
store the calculated relative blood pressure value.

32. The system as recited in claim 31, wherein the backend computing system comprises a database accessible by one or more health care providers, and wherein the one or more health care providers can obtain the relative physiologic parameter value from the database and use the relative physiologic parameter value to provide a service to the patient selected from the group consisting of diagnosing the patient, prescribing medication to the patient, providing a therapy to the patient, or modifying one or more settings of the IMD.

* * * * *